US012774770B2

(12) United States Patent
Fujita et al.

(10) Patent No.: US 12,774,770 B2
(45) Date of Patent: Oct. 27, 2026

(54) CONDUIT CONNECTION DEVICE FOR AN INSERTION-INSTRUMENT AND ENDOSCOPE APPARATUS

(71) Applicant: OLYMPUS MEDICAL SYSTEMS CORP., Tokyo (JP)

(72) Inventors: Naoyuki Fujita, Hachioji (JP); Takumi Kawakami, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 539 days.

(21) Appl. No.: 18/214,641

(22) Filed: Jun. 27, 2023

(65) Prior Publication Data

US 2023/0414073 A1 Dec. 28, 2023

Related U.S. Application Data

(60) Provisional application No. 63/356,055, filed on Jun. 28, 2022.

(51) Int. Cl.
*F16L 37/56* (2006.01)
*A61B 1/00* (2006.01)
(Continued)

(52) U.S. Cl.
CPC .......... *F16L 37/56* (2013.01); *A61B 1/00119* (2013.01); *A61B 1/00128* (2013.01);
(Continued)

(58) Field of Classification Search
CPC . F16L 35/00; F16L 37/56; F16L 39/02; F16L 39/00; F16L 2201/10;
(Continued)

(56) References Cited

U.S. PATENT DOCUMENTS 3,469,863 A * 9/1969 Riester .................... F16L 37/56
4,150,673 A 4/1979 Watt
(Continued)

FOREIGN PATENT DOCUMENTS

CN 113243878 A 8/2021
CN 113677253 A 11/2021
(Continued)

OTHER PUBLICATIONS

Office Action (CN OA1) dated Jul. 13, 2026, issued in corresponding Chinese Patent Application No. 202310750465.8.
(Continued)

*Primary Examiner* — William S. Choi
(74) *Attorney, Agent, or Firm* — Morgan, Lewis & Bockius LLP

(57) ABSTRACT

A conduit connection device comprises a plurality of fluid circulation lines, each of the plurality of fluid circulation lines having a conduit, a plurality of relay fluid circulation lines, each of the plurality of relay fluid circulation lines having a relay fluid conduit, a plurality of conduit connectors, and interference components are attached to the conduit connectors such that, in a first connection combination, the conduit connectors on a first end of each of the plurality of fluid circulation lines cooperate with the conduit connectors on a first end of each of the plurality of relay fluid circulation lines to connect respective fluid circulation lines to respective relay fluid circulation lines, and wherein, in other than the first connection combination, the plurality of interference components prevent connecting at least one of the plurality of fluid circulation lines to at least one of the plurality relay fluid circulation lines.

15 Claims, 16 Drawing Sheets

(51) Int. Cl.
*A61B 1/005* (2006.01)
*A61B 1/12* (2006.01)
*A61M 39/10* (2006.01)
*F16L 39/02* (2006.01)

(52) U.S. Cl.
CPC ............... *A61B 1/005* (2013.01); *A61B 1/126* (2013.01); *A61M 2039/1083* (2013.01); *F16L 39/02* (2013.01)

(58) Field of Classification Search
CPC .. A61M 2039/1083; A61M 2039/1088; A61M 39/105
See application file for complete search history.

(56) References Cited

U.S. PATENT DOCUMENTS

| | | | | |
|---|---|---|---|---|
| 4,478,436 | A * | 10/1984 | Hashimoto | F16L 39/02 |
| 4,754,993 | A * | 7/1988 | Kraynick | F16L 37/56 |
| 4,900,065 | A * | 2/1990 | Houck | F16L 37/56 |
| 4,982,736 | A * | 1/1991 | Schneider | F16L 37/56 |
| 5,217,432 | A * | 6/1993 | Rudzena | |
| 5,219,185 | A * | 6/1993 | Oddenino | F16L 37/56 |
| 6,569,087 | B2 | 5/2003 | Naito et al. | |
| 7,484,769 | B2 * | 2/2009 | Domash | |
| 8,092,409 | B2 * | 1/2012 | Mros | F16L 37/56 |
| 8,256,459 | B2 * | 9/2012 | Tesluk | F16L 37/56 |
| 9,151,425 | B2 * | 10/2015 | Faram | F16L 37/56 |
| 10,998,665 | B2 * | 5/2021 | McKevitt | A61M 39/105 |
| 11,168,822 | B2 * | 11/2021 | Lee | F16L 37/56 |
| 11,415,251 | B2 * | 8/2022 | Johnson | A61M 39/105 |
| 12,070,554 | B2 * | 8/2024 | Mallikarjunagoud | F16L 37/56 |
| 2003/0034649 | A1 * | 2/2003 | Gault | |
| 2007/0142706 | A1 | 6/2007 | Matsui et al. | |
| 2007/0260113 | A1 | 11/2007 | Otawara | |
| 2013/0267779 | A1 | 10/2013 | Woolford et al. | |
| 2014/0191501 | A1 | 7/2014 | Brugger et al. | |
| 2014/0364692 | A1 | 12/2014 | Salman et al. | |
| 2017/0215964 | A1 | 8/2017 | Harrah et al. | |
| 2019/0225207 | A1 * | 7/2019 | Vanstone | |
| 2020/0187768 | A1 | 6/2020 | Shelton et al. | |
| 2021/0068616 | A1 | 3/2021 | Sato | |
| 2021/0085158 | A1 | 3/2021 | Ikuma et al. | |
| 2021/0228064 | A1 | 7/2021 | Sørensen et al. | |
| 2023/0383878 | A1 * | 11/2023 | Rademacher | F16L 37/56 |
| 2025/0302285 | A1 | 10/2025 | Hiraga et al. | |

FOREIGN PATENT DOCUMENTS

| | | | |
|---|---|---|---|
| EP | 2724659 | A1 | 4/2014 |
| JP | 3368180 | B2 | 1/2003 |
| JP | 3488170 | B2 | 1/2004 |
| JP | 2006-187547 | A | 7/2006 |
| JP | 2007-167302 | A | 7/2007 |
| JP | 2009-142531 | A | 7/2009 |
| JP | 2013-106711 | A | 6/2013 |
| WO | 2006/098073 | A1 | 9/2006 |
| WO | 2019/176131 | A1 | 9/2019 |
| WO | 2019/176171 | A1 | 9/2019 |
| WO | 2023/286241 | A1 | 1/2023 |
| WO | 2023/026447 | A1 | 3/2023 |

OTHER PUBLICATIONS

Office Action (CN OA2) dated Jul. 30, 2026, issued in corresponding Chinese Patent Application No. 202310777669.0.

Office Action dated Aug. 21, 2026, issued in corresponding Chinese Patent Application No. 202310749543.2.

* cited by examiner

CONDUIT CONNECTION DEVICE FOR AN INSERTION-INSTRUMENT AND ENDOSCOPE APPARATUS

RELATED APPLICATION DATA

This application is based on and claims priority under 35 U.S.C. § 119 to U.S. Provisional Application No. 63/356,055 filed on Jun. 28, 2022, the entire contents of which are incorporated herein by reference.

BACKGROUND

The present disclosure relates to a connection device including conduit connectors of a plurality of fluid circulation conduits connecting an insertion instrument.

Conventionally, an endoscope has been widely used in, for example, medical and industrial fields. A medical endoscope used in the medical field has a function to acquire an image of a lesion site inside an organ or the like by inserting an insertion portion including an image pickup unit into a body cavity of a living body. The image thus acquired is used, for example, for image diagnosis through observation or examination of the lesion site or the like.

Such endoscopes include an endoscope in which a plurality of conduits for circulation of fluid such as liquid or gas are inserted between an operation portion and a distal end portion of an insertion portion. The plurality of conduits are, for example, water feeding channels or suction channels.

A water feeding channel is a conduit provided to supply cleaning water for cleaning a front surface of an observation window provided at a distal end portion of the endoscope. The water feeding channel has such a configuration in which a predetermined liquid is supplied through a predetermined fluid circulation conduit connected to an external fluid circulation device.

A suction channel is a conduit that communicates with a suction opening provided at the distal end portion of the endoscope and is provided to collect a predetermined target object in a body cavity by suctioning. The suction channel has such a configuration in which suction can be performed through a predetermined fluid circulation conduit connected to an external fluid circulation device.

In an endoscope including such a suction channel, in particular, in an endoscope that mainly suctions a hard target object such as a crushed calculus piece, the suction channel is clogged with the target object being suctioned in some cases.

Thus, some endoscopes of this kind have a configuration for resolving clogging of the suction channel with a target object. In an endoscope with such a configuration, for example, a bifurcation channel bifurcating from the suction channel is additionally provided and connected to an external fluid circulation device such as a syringe or a pump for resolving suction clogging.

In an endoscope with such a configuration, at least three channels are provided. In an endoscope apparatus including the endoscope with such a configuration, connection between each channel and an external fluid circulation device tends to become more complicated as the number of provided channels increases.

Various kinds of disclosures are proposed by, for example, Japanese Patent No. 3368180 and Japanese Patent Application Laid-Open Publication No. 2007-167302 as configurations of a conventional endoscope.

An endoscope disclosed by Japanese Patent No. 3368180 described above includes an air feeding conduit and another conduit. The endoscope also includes a plurality of conduit connectors that connect these conduits to an external fluid supply device.

For example, an endoscope disclosed by Japanese Patent Application Laid-Open Publication No. 2007-167302 described above includes a first communication path and a second communication path. A first connection part that is connected to a fluid supply device is formed at an end part of the first communication path. A second connection part that is connected to the fluid supply device is formed at an end part of the second communication path.

SUMMARY

A conduit connection device according to an aspect of the present disclosure includes a plurality of fluid circulation lines, each of the plurality of fluid circulation lines having a conduit, a plurality of relay fluid circulation lines, each of the plurality of relay fluid circulation lines having a relay fluid conduit, a plurality of conduit connectors, and a plurality of interference components. A first end of each of the plurality of fluid circulation lines has one of the plurality of conduit connectors attached thereto, wherein a first end of each of the plurality of relay fluid circulation lines has one of the plurality of conduit connectors attached thereto. The conduit connectors on the first end of each of the plurality of fluid circulation lines are configured to cooperate with the conduit connectors on the first end of each of the plurality of relay fluid circulation lines to form a connection. The plurality of interference components are attached to the plurality of conduit connectors such that, in a first connection combination, the conduit connectors on the first end of each of the plurality of fluid circulation lines cooperate with the conduit connectors on the first end of each of the plurality of relay fluid circulation lines to connect respective fluid circulation lines to respective relay fluid circulation lines. In other than the first connection combination, the plurality of interference components prevent connecting at least one of the plurality of fluid circulation lines to at least one of the plurality relay fluid circulation lines.

An endoscope apparatus according to an aspect of the present disclosure includes an endoscope, a plurality of fluid circulation lines connecting the endoscope and an external fluid circulation device, the plurality of fluid circulation lines each including a relay part, a plurality of conduit connectors, and a plurality of interference components. The plurality of interference components are attached to the plurality of conduit connectors such that, in a first connection combination, each of the plurality of conduit connectors are attached to a respective relay part of the plurality of fluid circulation lines, and, in other than the first connection combination, at least one of the plurality of conduit connectors are prevented from being attached in a second connection combination.

DETAILED DESCRIPTION

Figure 1:
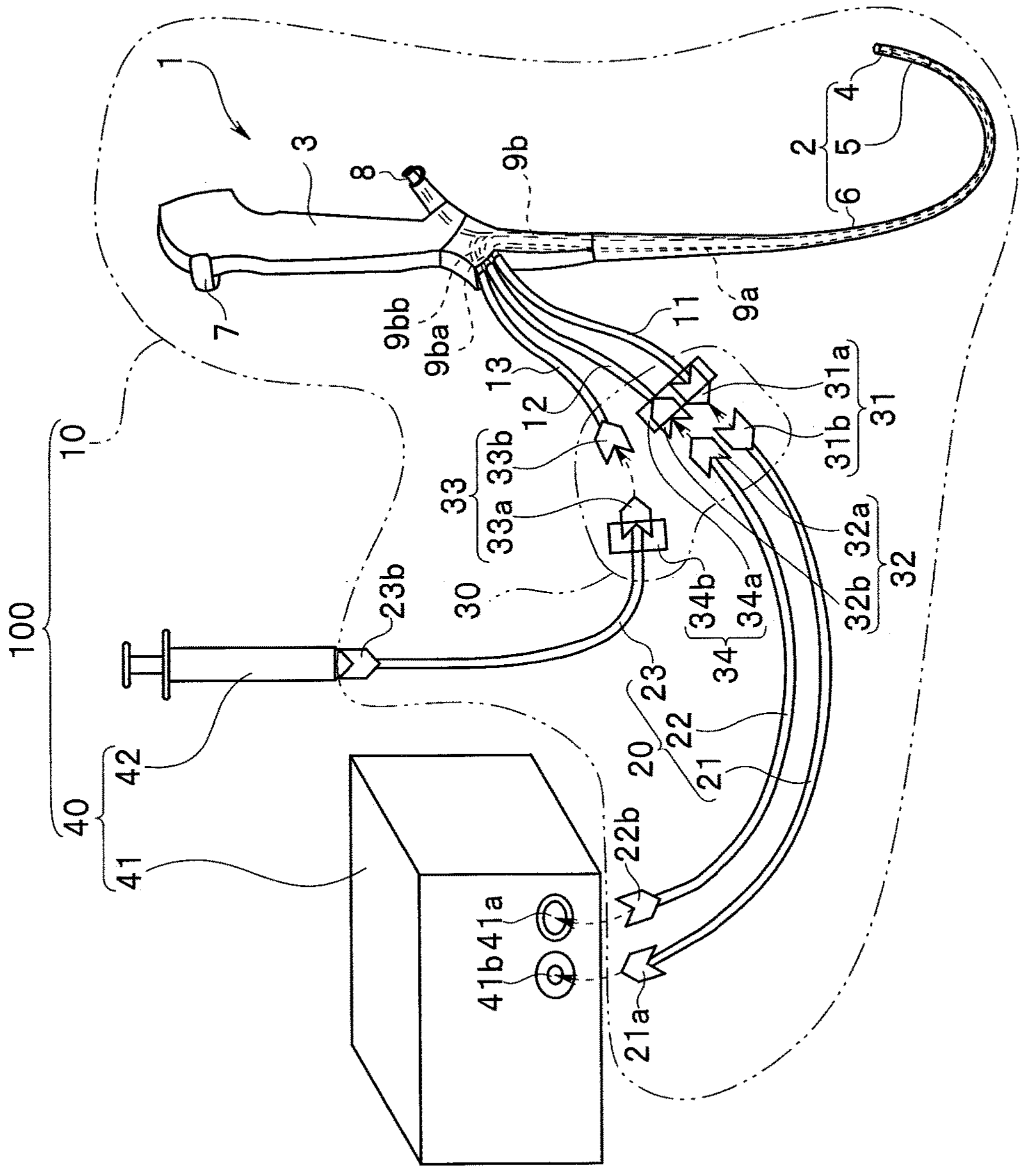
FIG. 1 is a system configuration diagram illustrating a schematic configuration of an endoscope system including an endoscope apparatus to which an insertion-instrument conduit connection device according to a first embodiment of the present disclosure is applied.

In a medical endoscope, a conduit connection component such as a connector including a Luer taper called a Luer lock (trademark) or the like is used as a fluid circulation conduit connector connecting a channel extending from an operation portion and an external fluid circulation device. In this case, it is possible to prevent wrong connection of conduits to some extent through appropriate disposition of male and female shapes of the Luer taper.

In an endoscope including at least three channels, the channels may be difficult to be reliably handled only through appropriate disposition of the male and female shapes of a Luer taper.

It might be difficult to visually reliably check the identification means in some cases, depending on, for example, an environment or situation in which an endoscope is used.

An endoscope including at least three conduits and using standard conduit connection components in male and female shapes may be difficult to reliably prevent wrong connection of a plurality of conduits.

According to embodiments of the present disclosure described below, it is possible to provide an insertion-instrument conduit connection device and an endoscope apparatus to which the insertion-instrument conduit connection device is applied, the insertion-instrument conduit connection device including, for example, a conduit connector of a plurality of fluid circulation conduits connecting an insertion instrument such as an endoscope including at least three channels to an external fluid circulation device, the insertion-instrument conduit connection device being capable of reliably preventing wrong physical connection by using a standard conduit connector.

The present disclosure will be described below with reference to illustrated embodiments. Each drawing used in the following description is schematically illustrated, and dimensional relations, scaling, and the like among members are illustrated differently for each constituent component in some cases to indicate the constituent component in a size enough to allow recognition on the drawing. Thus, in the present disclosure, for example, the number of constituent components, a shape of each constituent component, a size ratio of the constituent components, and a relative positional relation among the constituent components illustrated in each drawing are not limited to illustrated forms.

First, an entire schematic configuration of an endoscope system including an endoscope apparatus to which an insertion-instrument conduit connection device of the present disclosure is applied will be described below with reference to FIG. 1 before detail description of insertion-instrument conduit connection devices according to embodiments of the present disclosure. FIG. 1 is a system configuration diagram illustrating an entire schematic configuration of an endoscope system including an endoscope apparatus to which an insertion-instrument conduit connection device according to a first embodiment of the present disclosure is applied.

As illustrated in FIG. 1, an endoscope system 100 including an endoscope apparatus 10 to which an insertion-instrument conduit connection device 30 according to the first embodiment of the present disclosure is applied includes the endoscope apparatus 10 and an external fluid circulation device 40.

The endoscope apparatus 10 includes an endoscope 1 as an insertion instrument, relay fluid circulation conduits 20, and the insertion-instrument conduit connection device 30.

The endoscope 1 includes an insertion portion 2 and an operation portion 3. The insertion portion 2 is formed in an elongated tube shape having flexibility as a whole. The insertion portion 2 includes a distal end portion 4, a bending portion 5, and a flexible tube portion 6 that are continuously provided in order from a distal end side.

A plurality of conduits (channels) are inserted and disposed inside the insertion portion 2 from the distal end portion 4 to inside of the operation portion 3. The plurality of conduits are, for example, a water feeding channel 9*a* and a suction channel 9*b*.

One end of the water feeding channel 9*a* is connected to a water feeding nozzle (not illustrated) formed at a distal end surface of the distal end portion 4. The other end of the water feeding channel 9*a* is connected to a water feeding conduit 11 (first conduit) externally extending from the operation portion 3.

One end of the suction channel 9*b* is connected to a distal end opening (not illustrated) formed at the distal end surface of the distal end portion 4. The other end of the suction channel 9*b* is connected to a forceps plug 8 disposed toward outside from the operation portion 3.

Bifurcation channels 9*ba* and 9*bb* bifurcating from a site closer to the operation portion 3 are formed in the suction channel 9*b*. The bifurcation channel 9*ba* is connected to a suction conduit 12 (second conduit) externally extending from the operation portion 3. The bifurcation channel 9*bb* is connected to a suction clogging resolution conduit 13 (third conduit) externally extending from the operation portion 3.

Note that parts of a plurality of conduit connectors (31, 32, and 33) are disposed at ends of the water feeding conduit 11, the suction conduit 12, and the suction clogging resolution conduit 13, respectively. Detailed configurations of the conduit connectors (31, 32, and 33) will be described later.

The operation portion 3 is a component that also serves as a grip portion grasped by a user of the endoscope 1 when using the endoscope 1. Various operation members are provided on an outer surface of the operation portion 3. FIG. 1 illustrates a bending operation lever 7 with which an operation for actively bending the bending portion 5 is performed. Note that FIG. 1 omits illustration of any other operation member to avoid complication of the drawing.

The forceps plug 8 is provided at a site closer to a distal end of the operation portion 3. The forceps plug 8 is a lid member with which an opening (not illustrated) communicating with the suction channel 9*b* can be opened and closed. When a non-illustrated treatment instrument is inserted through the opening of the forceps plug 8, the treatment instrument can externally protrude forward from the distal end opening of the distal end portion 4 of the insertion portion 2 through the suction channel 9*b* and be disposed. In this case, the suction channel 9*b* functions as a treatment instrument insertion channel.

Note that the endoscope 1 is assumed to be what is called a small-diameter endoscope used for observation or various treatments of inside of an urethra, a prostate, inside of a bladder, or the like with the insertion portion 2 being inserted into a body cavity of a patient through, for example, an urethral opening of the patient. The endoscope 1 has the same configuration as a conventional endoscope of the same kind. Thus, detailed description of the configuration is omitted. The endoscope 1 is also assumed to be, for example, what is called a single-use endoscope that is discarded after use. However, the present disclosure is not limited to such an endoscope, but the endoscope 1 may be assumed to be what is called a reuse endoscope that is repeatedly usable through sterilization and cleaning after use.

The relay fluid circulation conduits 20 include, for example, at least three fluid circulation conduits of a first relay conduit 21, a second relay conduit 22, and a third relay conduit 23 (a plurality of relay fluid circulation lines).

One end (first end) of the first relay conduit 21 is connected to the water feeding conduit 11 connected to the water feeding channel 9*a*. The other end of the first relay conduit 21 is connected to a predetermined connection port (refer to a reference sign 41*b* in FIG. 1) of the external fluid circulation device 40.

Similarly, one end (first end) of the second relay conduit 22 is connected to the suction conduit 12 connected to the bifurcation channel 9*ba* of the suction channel 9*b*. The other end of the second relay conduit 22 is connected to a predetermined connection port (refer to a reference sign 41*a* in FIG. 1) of the external fluid circulation device 40.

Similarly, one end (first end) of the third relay conduit 23 is connected to the suction clogging resolution conduit 13 connected to the bifurcation channel 9*bb* of the suction channel 9*b*. The other end of the third relay conduit 23 is connected to a predetermined instrument (refer to a reference sign 42 in FIG. 1) of the external fluid circulation device 40.

Figure 2:
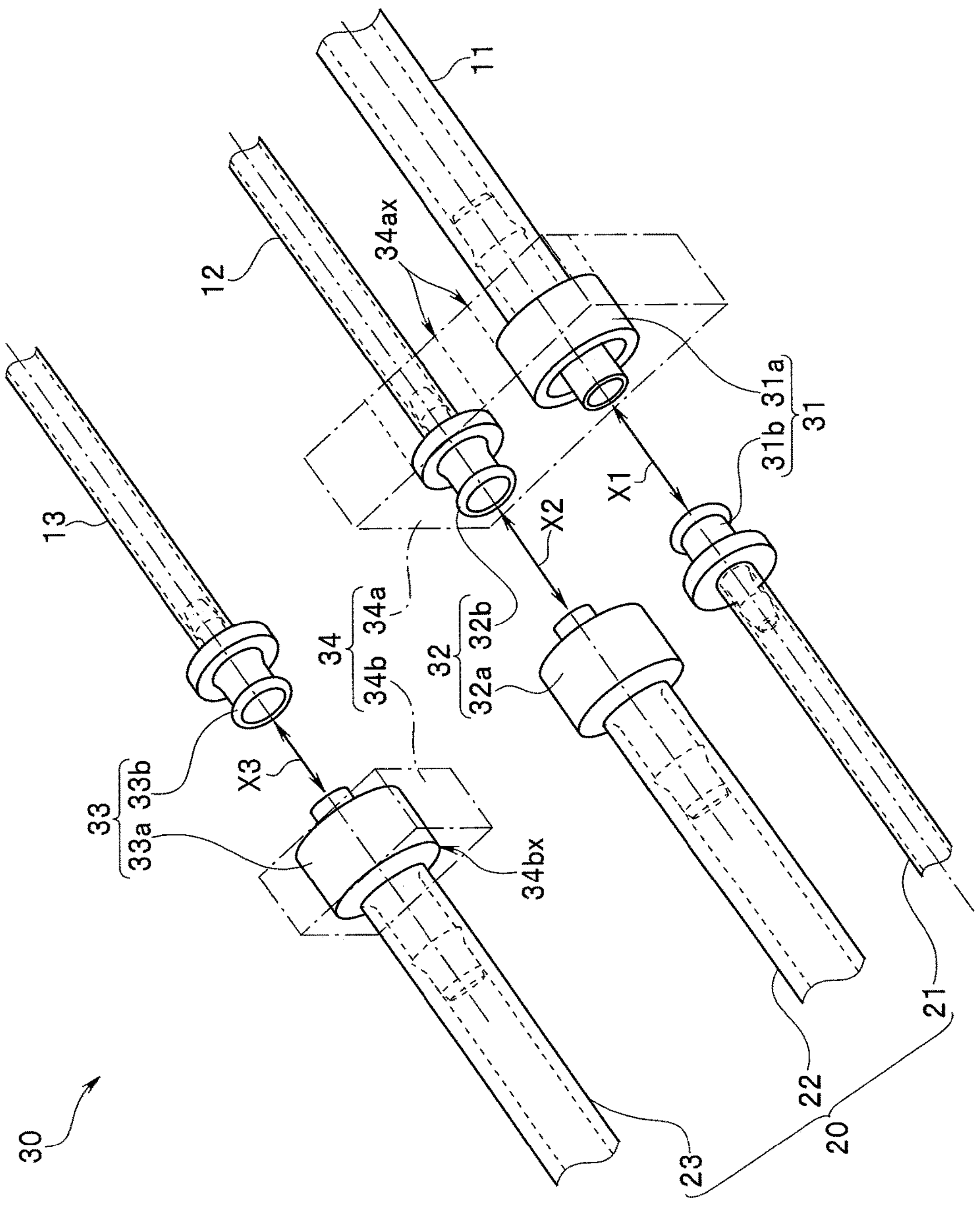
FIG. 2 is a schematic configuration diagram illustrating the insertion-instrument conduit connection device according to the first embodiment of the present disclosure in an enlarging manner.

Note that the one end of each of the relay conduits (21, 22, and 23) of the relay fluid circulation conduits 20 is connected to the corresponding one of the conduits (11, 12, and 13) through the insertion-instrument conduit connection device 30. Specifically, the water feeding conduit 11 and the first relay conduit 21, the suction conduit 12 and the second relay conduit 22, and the suction clogging resolution conduit 13 and the third relay conduit 23 extend in a long axis direction, and the conduit connectors (31, 32, and 33) are connected halfway through the corresponding conduits. FIG. 2 is a schematic configuration diagram illustrating the insertion-instrument conduit connection device according to the first embodiment of the present disclosure in an enlarging manner.

As illustrated in FIGS. 1 and 2, the insertion-instrument conduit connection device 30 includes the plurality of conduit connectors (31, 32, and 33) and a plurality of interference components 34.

The plurality of conduit connectors are conduit connection components attached to respective relay parts of a plurality of fluid circulation conduits (a plurality of fluid circulation lines having a conduit) connecting the endoscope 1 and the external fluid circulation device 40 (to be described later in details). In other words, a first end of each of the plurality of fluid circulation lines has one of the plurality of conduit connectors attached thereto and a first end of each of the plurality of relay fluid circulation lines has one of the plurality of conduit connectors attached thereto. The plurality of fluid circulation conduits are constituted by the relay conduits (21, 22, and 23) of the relay fluid circulation conduits 20 and the water feeding conduit 11, the suction conduit 12, and the suction clogging resolution conduit 13. The first relay conduit 21 and the water feeding conduit 11 are collectively referred to as a first fluid circulation conduit. The second relay conduit 22 and the suction conduit 12 are collectively referred to as a second fluid circulation conduit. The third relay conduit 23 and the suction clogging resolution conduit 13 are collectively referred to as a third fluid circulation conduit.

The plurality of conduit connectors are at least three conduit connectors of a first conduit connector 31, a second conduit connector 32, and a third conduit connector 33. Each of the plurality of conduit connectors (31, 32, and 33) is constituted by a pair of a connection body (a first connection body 31*a*, a second connection body 32*a*, or a third connection body 33*a*) as a male plug and a connection counterpart body (a first counterpart body 31*b*, a second counterpart body 32*b*, and a third counterpart body 33*b*) as a female plug connected to the connection body (31*a*, 32*a*, and 33*a*).

Note that, as illustrated in FIG. 2, standard conduit connection components such as connectors each including a Luer taper called a Luer lock (trademark) or the like are applied as the plurality of conduit connectors in the present embodiment. Illustration of the plurality of conduit connectors (31, 32, and 33) is as exemplarily illustrated in FIG. 2. However, in any drawing such as FIG. 1 other than FIG. 2, the illustration is made in a simplified form to avoid complication of the drawing. In FIG. 2, to clearly indicate a disposition relation among the conduit connectors (31, 32, and 33) and the corresponding interference component 34, the conduit connectors (31, 32, and 33) are clearly illustrated with solid lines and the interference component 34 is illustrated with dashed and single-dotted lines.

In the present embodiment, the first conduit connector 31 is constituted by a pair of a connection body 31*a* and a connection counterpart body 31*b*. The connection body 31*a* is provided at an end of the water feeding conduit 11. The connection counterpart body 31*b* is provided at one end (first end) of the first relay conduit 21. The connection body 31*a* and the connection counterpart body 31*b* are connected to each other in an arrow X1 direction in FIG. 2.

In the present embodiment, the second conduit connector 32 is constituted by a pair of a connection body 32*a* and a connection counterpart body 32*b*. The connection body 32*a* is provided at one end (first end) of the second relay conduit 22. The connection counterpart body 32*b* is provided at an end of the suction conduit 12. The connection body 32*a* and the connection counterpart body 32*b* are connected to each other in an arrow X2 direction in FIG. 2.

In the present embodiment, the third conduit connector 33 is constituted by a pair of a connection body 33*a* and a connection counterpart body 33*b*. The connection body 33*a* is provided at one end (first end) of the third relay conduit 23. The connection counterpart body 33*b* is provided at an end of the suction clogging resolution conduit 13. The connection body 33*a* and the connection counterpart body 33*b* are connected to each other in an arrow X3 direction in FIG. 2.

In this manner, in the insertion-instrument conduit connection device 30 according to the present embodiment, the first conduit connector 31 and the second conduit connector 32 have orientations different from each other or have configurations different from each other. The second conduit connector 32 and the third conduit connector 33 have the same orientation or have the same configuration.

The orientation or configuration of a conduit connector indicates disposition of the connection body (male plug) and the connection counterpart body (female plug).

Specifically, for example, in the first conduit connector 31, the connection body 31*a* is provided at the end of the water feeding conduit 11 (on the endoscope 1 side) and the connection counterpart body 31*b* is provided at the one end of the first relay conduit 21 (on the external fluid circulation device 40 side).

In the second conduit connector 32, the connection body 32*a* is provided at the one end of the second relay conduit 22 (on the external fluid circulation device 40 side) and the connection counterpart body 32*b* is provided at the end of the suction conduit 12 (on the endoscope 1 side).

In the third conduit connector 33, the connection body 33*a* is provided at the one end of the third relay conduit 23 (on the external fluid circulation device 40 side) and the connection counterpart body 33*b* is provided at the end of the suction clogging resolution conduit 13 (on the endoscope 1 side).

Accordingly, in the present embodiment, the first conduit connector 31 and the second conduit connector 32 have orientations or configurations different from each other. The second conduit connector 32 and the third conduit connector 33 have the same orientation or the same configuration.

Note that, as illustrated in FIG. 1, a male connector 21*a* having the same form as the connection bodies of the conduit connectors is provided at the other end of the first relay conduit 21. A female connector 22*b* having the same form as the connection counterpart bodies of the conduit connectors is provided at the other end of the second relay conduit 22. A female connector 23*b* having the same form as the connection counterpart bodies of the conduit connectors is provided at the other end of the third relay conduit 23.

The plurality of interference components 34 are components having a function not to interfere with the plurality of conduit connectors in correct connection combination but to selectively interfere with the conduit connectors in wrong connection combination to interrupt predetermined connection when the plurality of interference components 34 are attached to the plurality of conduit connectors, respectively.

As illustrated in FIG. 2, each of the plurality of interference components 34 is constituted by a fixation member 34*a* and an interference member 34*b*. The fixation member 34*a* is a member having a function to adjacently hold and fix the connection body 31*a* of the first conduit connector 31 and the connection counterpart body 32*b* of the second conduit connector 32 in parallel. Thus, the fixation member 34*a* is provided with a plurality of holes 34*ax* into which the first fluid circulation conduit (11 and 21) and the second fluid circulation conduit (12 and 22) are inserted or the first conduit connector 31 and the second conduit connector 32 are inserted.

The interference member 34*b* is provided at the connection body 33*a* of the third conduit connector 33. Thus, the interference member 34*b* is provided with a hole 34*bx* into which the third fluid circulation conduit (13 and 23) or the third conduit connector 33 is inserted.

The interference member 34*b* has a function to interrupt connection of one of the first conduit connector 31 and the second conduit connector 32 when the other of the first conduit connector 31 and the second conduit connector 32 is connected to the third conduit connector 33. Thus, an outer shape of the interference member 34*b* has a larger diameter than an outer shape of the connection body (31*a*, 32*a*, or 33*a*) or connection counterpart body (31*b*, 32*b*, and 33*b*) of each conduit connector (31, 32, or 33) (to be described later in details; refer to FIGS. 3 to 6, for example). Note that although the outer shape of the interference member 34*b* is described above by using the phrase "larger diameter", a sectional shape of the interference member 34*b* is not limited to, for example, a substantially circular shape. For example, the outer shape of the interference member 34*b* may have a sectional shape larger than the outer shape of each connection body (31*a*, 32*a*, or 33*a*) or each connection counterpart body (31*b*, 32*b*, or 33*b*).

In other words, the outer shape of the interference member 34*b* has a wider diameter than the outer shape of the connection body (31*a*, 32*a*, or 33*a*) or connection counterpart body (31*b*, 32*b*, and 33*b*) of each conduit connector (31, 32, or 33). The phrase "wider diameter" for the outer shape of the interference member 34*b* does not limit the sectional shape of the interference member 34*b* to a substantially circular shape as described above. In this manner, the outer shape of the interference member 34*b* is designed to have a sectional shape larger than the outer shape of each connection body (31*a*, 32*a*, or 33*a*) or each connection counterpart body (31*b*, 32*b*, or 33*b*), and thus, when wrongly connected, a connection body (the connection body 33*a* in the present configuration example) provided with the interference member 34*b* has a small interval to a connection body and a connection counterpart body (the connection body 31*a* and the connection counterpart body 31*b* in the present configuration example) that are adjacent to the connection body (33*a*). Accordingly, the interference member 34*b* interrupts connection of the connection body (31*a*) and the connection counterpart body (31*b*) adjacent to the connection body (33*a*) (details of workings will be described later).

Figure 3:
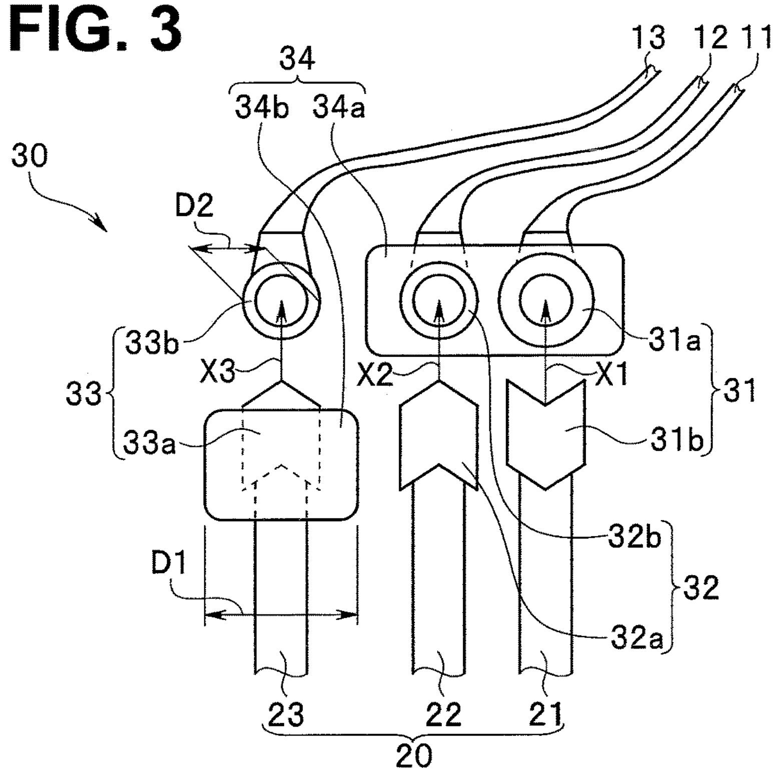
FIG. 3 is a schematic diagram for description of workings of the insertion-instrument conduit connection device according to the first embodiment of the present disclosure, illustrating correct connection combination of conduit connectors before connection.

For example, a reference sign D1 illustrated in FIG. 3 represents a dimension of the outer shape of the interference member 34*b*. A reference sign D2 illustrated in FIG. 3 represents a dimension of the outer shape of the connection body or connection counterpart body of each conduit connector. Note that the reference sign D2 illustrated in FIG. 3 exemplarily represents the dimension of the outer shape of the connection counterpart body 33*b* of the third conduit connector 33. The outer shape D1 of the interference member 34*b* and the outer shape D2 of the connection body or connection counterpart body of each conduit connector are set to satisfy D1>D2.

Returning to FIG. 1, the external fluid circulation device 40 is an external instrument of various kinds connected to the endoscope 1 through the plurality of fluid circulation conduits. The external fluid circulation device 40 is, for example, an air/water feeding supply device 41 or a syringe 42. Note that the external fluid circulation device 40 may have any other form. For example, a pump device (not illustrated) in a predetermined form may be applied in place of the syringe 42.

An air/water feeding supply device in a typical form is applied as the air/water feeding supply device 41. The air/water feeding supply device 41 is provided with a plurality of connection ports (41*a* and 41*b*). The male connector 21*a* provided at the other end of the first relay conduit 21 is connected to the first connection port 41*b* of the air/water feeding supply device 41. The female connector 22*b* provided at the other end of the second relay conduit 22 is connected to the second connection port 41*a* of the air/water feeding supply device 41.

A syringe in a typical form is applied as the syringe 42. The female connector 23*b* provided at the other end of the third relay conduit 23 is connected to a connection port of the syringe 42.

Figure 4:
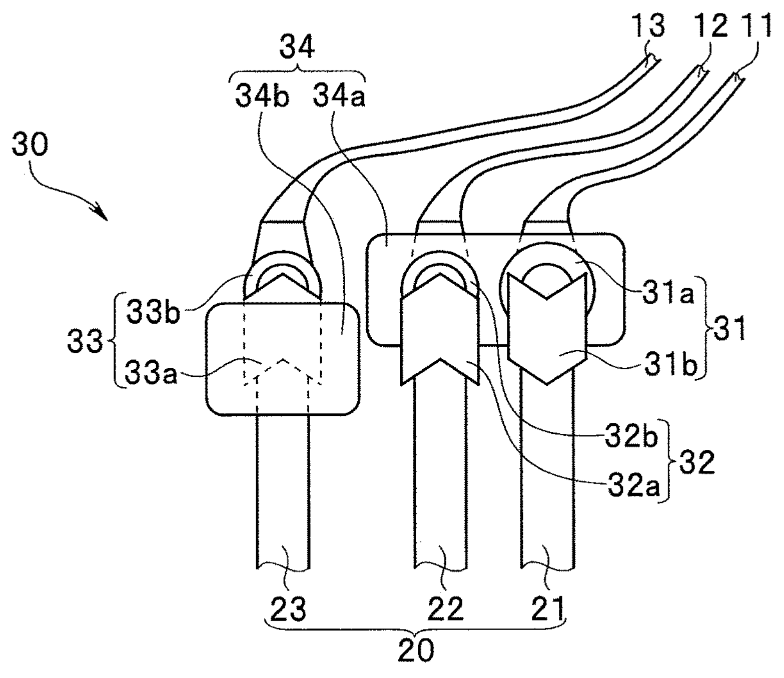
FIG. 4 is a schematic diagram for description of workings of the insertion-instrument conduit connection device according to the first embodiment of the present disclosure, illustrating correct connection combination of the conduit connectors when connected.
Figure 5:
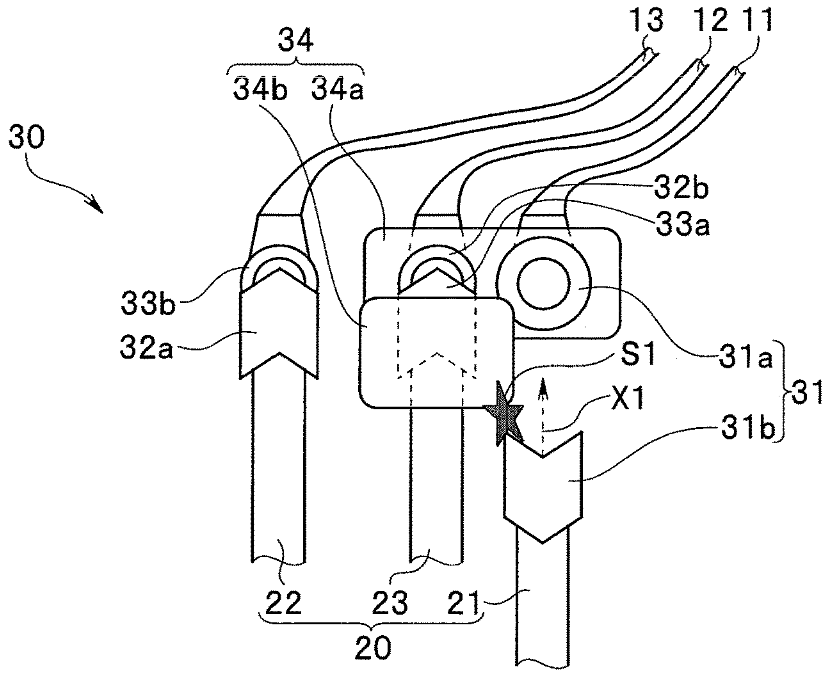
FIG. 5 is a schematic diagram for description of workings of the insertion-instrument conduit connection device according to the first embodiment of the present disclosure, illustrating a first example of wrong connection combination of the conduit connectors.
Figure 6:
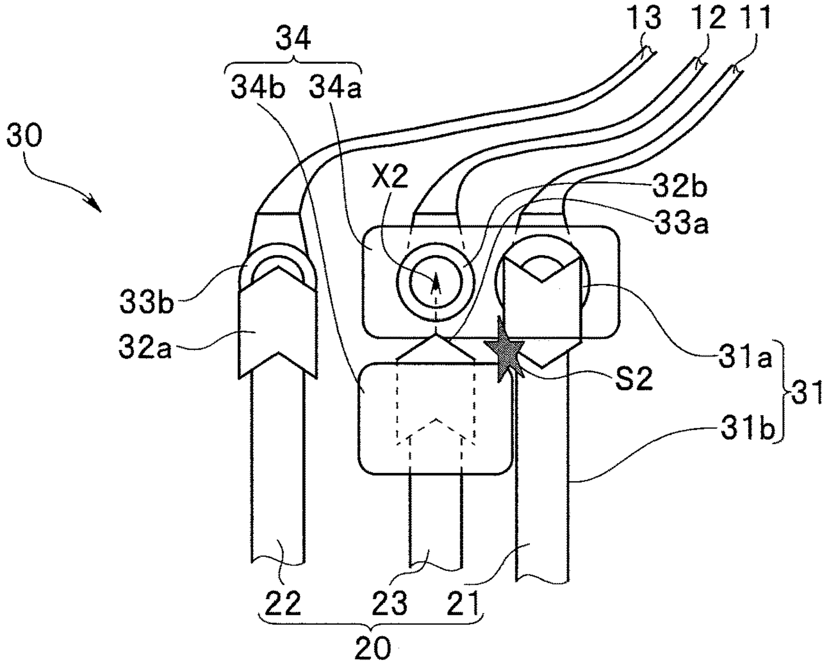
FIG. 6 is a schematic diagram for description of workings of the insertion-instrument conduit connection device according to the first embodiment of the present disclosure, illustrating a second example of wrong connection combination of the conduit connectors.

Workings of the insertion-instrument conduit connection device 30 according to the first embodiment of the present disclosure thus configured will be described below with reference to FIGS. 3 to 6. FIGS. 3 to 6 are each a schematic diagram for description of workings of the insertion-instrument conduit connection device according to the present embodiment. FIG. 3 illustrates correct connection combination of the conduit connectors (31, 32, and 33) of the insertion-instrument conduit connection device before connection. FIG. 4 illustrates correct connection combination of the conduit connectors (31, 32, and 33) of the insertion-instrument conduit connection device when connected. FIGS. 5 and 6 illustrate examples (first and second examples) of wrong connection combination of the conduit connectors (31, 32, and 33) of the insertion-instrument conduit connection device.

First, correct connection combination of the conduit connectors (31, 32, and 33) of the insertion-instrument conduit connection device 30 in the present embodiment will be described below.

The connection counterpart body 31*b* at the one end of the first relay conduit 21 is connected to the connection body 31*a* at the end of the water feeding conduit 11 (refer to an arrow X1 in FIG. 3). Accordingly, the first conduit connector 31 of the first fluid circulation conduit is connected.

The connection body 32*a* at the one end of the second relay conduit 22 is connected to the connection counterpart body 32*b* at the end of the suction conduit 12 (refer to an arrow X2 in FIG. 3). Accordingly, the second conduit connector 32 of the second fluid circulation conduit is connected.

The connection body 33*a* at the one end of the third relay conduit 23 is connected to the connection counterpart body 33*b* at the end of the suction clogging resolution conduit 13 (refer to the arrow X3 in FIG. 3). Accordingly, the third conduit connector 33 of the third fluid circulation conduit is connected.

In such correct connection combination, the interference component 34 interferes with none of the conduit connectors (31, 32, and 33) as illustrated in FIG. 4. Accordingly, the conduit connectors (31, 32, and 33) reliably ensure connection of the fluid circulation conduits.

Next, a case of wrong connection combination of the conduit connectors (31, 32, and 33) in the insertion-instrument conduit connection device 30 in the present embodiment is considered.

In the insertion-instrument conduit connection device 30 according to the present embodiment, the second conduit connector 32 and the third conduit connector 33 have the same orientation or the same configuration as described above. Thus, the connection body 33*a* of the third conduit connector 33 is potentially wrongly connected to the connection counterpart body 32*b* of the second conduit connector 32. Similarly, the connection body 32*a* of the second conduit connector 32 is potentially wrongly connected to the connection counterpart body 33*b* of the third conduit connector 33.

For example, as illustrated in FIG. 5, when the connection body 33*a* of the third conduit connector 33 is wrongly connected to the connection counterpart body 32*b* of the second conduit connector 32, the connection counterpart body 31*b* interferes with the interference member 34*b* at a position indicated by a reference sign 51 in FIG. 5 as connection of the connection counterpart body 31*b* to the connection body 31*a* of the first conduit connector 31 is attempted in the arrow X1 direction in FIG. 5. Accordingly, connection between the connection body 31*a* and the connection counterpart body 31*b* is interrupted. Thus, the user can recognize wrong connection.

For example, as illustrated in FIG. 6, when the connection counterpart body 31*b* of the first conduit connector 31 is correctly connected to the connection body 31*a* of the first conduit connector 31, the interference member 34*b* interferes with the connection counterpart body 31*b*, which is connected next, at a position indicated by a reference sign S2 in FIG. 6 as connection of the connection body 33*a* of the third conduit connector 33 to the connection counterpart body 32*b* of the second conduit connector 32 is attempted in the arrow X2 direction in FIG. 6. Accordingly, connection between the connection counterpart body 32*b* and the connection body 33*a* is interrupted. Thus, the user can recognize wrong connection.

In this manner, the interference member 34*b* interrupts connection of one of the first conduit connector 31 and the second conduit connector 32 when the third conduit connector 33 is connected to the other of the first conduit connector 31 and the second conduit connector 32.

Since the outer shape of the interference member 34*b* is formed to have a section larger than the outer shape of the connection body 33*a* of the third conduit connector 33 as described above, the interference member 34*b* interrupts connection of another conduit connector when wrong connection as illustrated in FIGS. 5 and 6 is performed.

As described above, according to the first embodiment, the insertion-instrument conduit connection device 30 includes the plurality of conduit connectors (31, 32, and 33) and the plurality of interference components 34. The interference components 34 do not interfere with the plurality of conduit connectors (31, 32, and 33) in correct connection combination but selectively interfere with the conduit connectors (31, 32, and 33) in wrong connection combination to interrupt connection.

Each of the plurality of conduit connectors (31, 32, and 33) is constituted by a pair of a connection body (31*a*, 32*a*, or 33*a*) as a male plug and a connection counterpart body (31*b*, 32*b*, or 33*b*) as a female plug that is connected to the connection body. Standard conduit connection components such as Luer tapers are applied as the plurality of conduit connectors (31, 32, and 33). Note that the plurality of conduit connectors are not limited to Luer tapers but may be conduit connection components in any other form.

In this case, the first conduit connector 31 provided at the first fluid circulation conduit and the second conduit connector 32 provided at the second fluid circulation conduit have orientations different from or configurations different from each other. The second conduit connector 32 and the third conduit connector 33 provided at the third fluid circulation conduit have the same orientation or have the same configuration.

Each of the interference components 34 is constituted by the fixation member 34*a* and the interference member 34*b*. The fixation member 34*a* adjacently holds and fixes the connection body 31*a* of the first conduit connector 31 and the connection counterpart body 32*b* of the second conduit connector 32 in parallel. The interference member 34*b* is provided at the connection body 33*a* of the third conduit connector 33. The outer shape of the interference member 34*b* is formed in a larger diameter (wider diameter) than the outer shape of the connection body 33*a*.

With such a configuration, the interference member 34*b* interrupts connection of the first conduit connector 31 when the second conduit connector 32 and the third conduit connector 33 are connected.

Accordingly, in the insertion-instrument conduit connection device 30 according to the present embodiment, the plurality of conduit connectors (31, 32, and 33) provided at relay parts of the plurality of fluid circulation conduits (11 and 21, 12 and 22, and 13 and 23) can be connected constantly in correct connection combination by using the plurality of conduit connectors (31, 32, and 33) in a standard form. Thus, with the insertion-instrument conduit connection device 30 according to the present embodiment, it is possible to reliably prevent wrong physical connection.

In the first embodiment described above, the fixation member 34*a* of each interference component 34 is provided with the plurality of holes 34*ax*. The plurality of holes 34*ax* are provided to adjacently hold and fix, to the fixation member 34*a*, the connection body 31*a* of the first conduit connector 31 and the connection counterpart body 32*b* of the second conduit connector 32 in parallel. Thus, the plurality of holes 34*ax* are formed to allow insertion of the first fluid circulation conduit (11 and 21) and the second fluid circulation conduit (12 and 22) or insertion of the first conduit connector 31 and the second conduit connector 32.

However, the form of the fixation member 34*a* of each interference component 34 is not limited to the form exemplarily described in the first embodiment described above.

Figure 7:
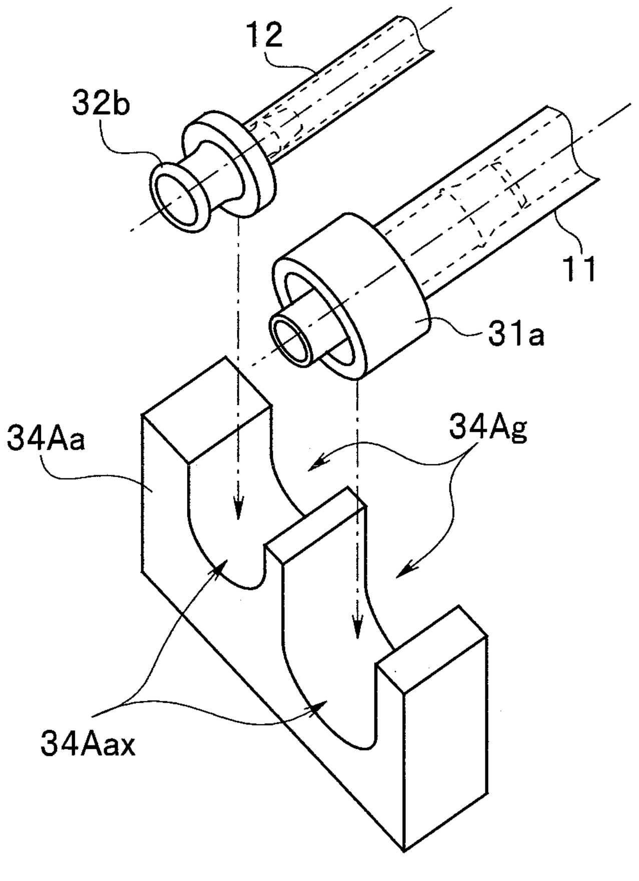
FIG. 7 is a diagram illustrating a modification of a fixation member of an interference component in the insertion-instrument conduit connection device according to the first embodiment of the present disclosure.

For example, a fixation member 34Aa in a form as illustrated in FIG. 7 may be applied in place of the fixation member 34*a* exemplarily described above in the first embodiment. FIG. 7 is a diagram illustrating a modification of the fixation member of each interference component in the insertion-instrument conduit connection device according to the first embodiment of the present disclosure.

As illustrated in FIG. 7, the fixation member 34Aa according to the present modification is provided with grooves 34Ag extending from an outer surface to holes 34Aax. Since the grooves 34Ag are provided at the fixation member 34Aa, the connection body 31*a* of the first conduit connector 31 and the connection counterpart body 32*b* of the second conduit connector 32 can be easily disposed, held, and fixed in the holes 34Aax of the fixation member 34Aa.

Figure 8:
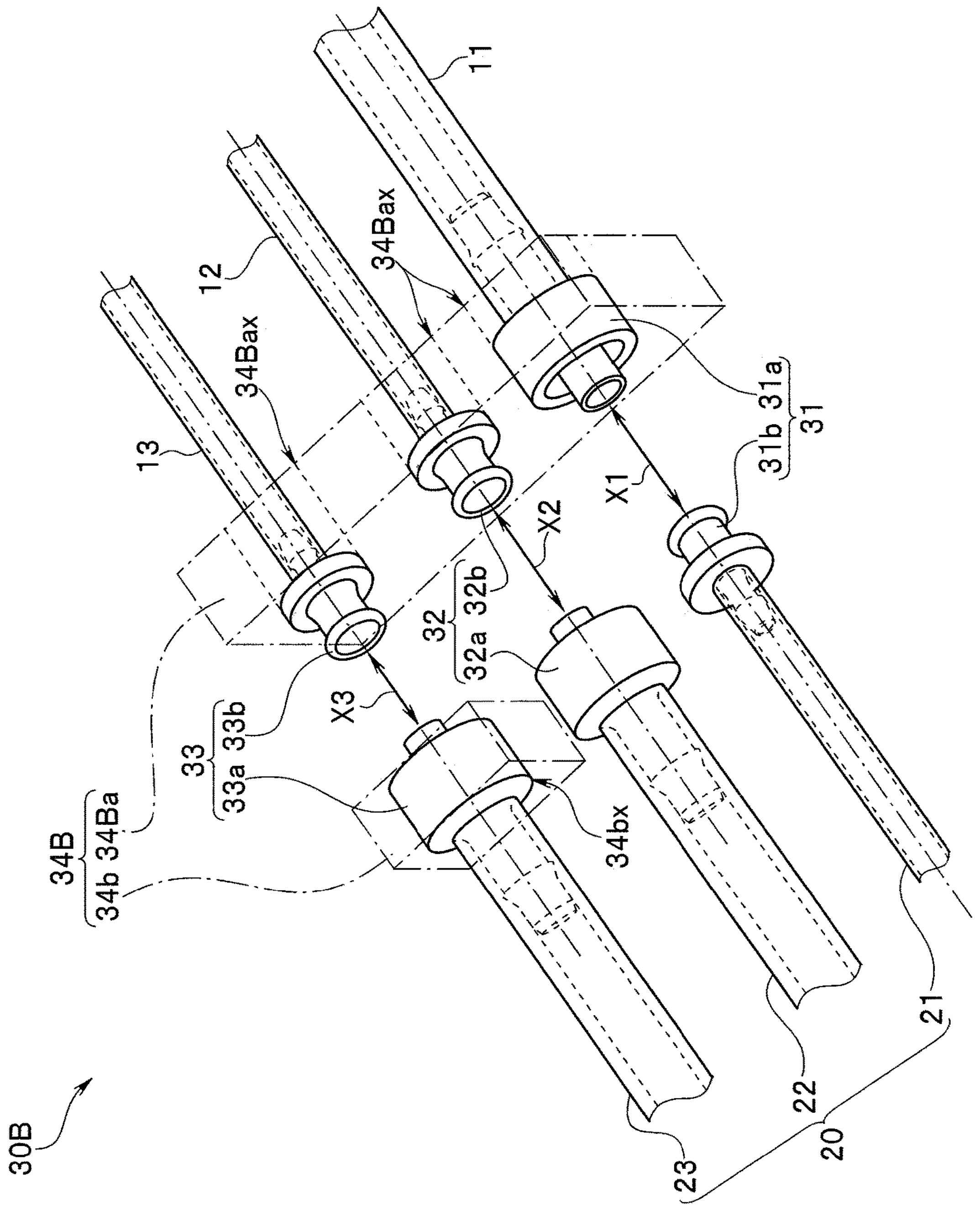
FIG. 8 is a schematic configuration diagram illustrating an insertion-instrument conduit connection device according to a second embodiment of the present disclosure in an enlarging manner.
Figure 9:
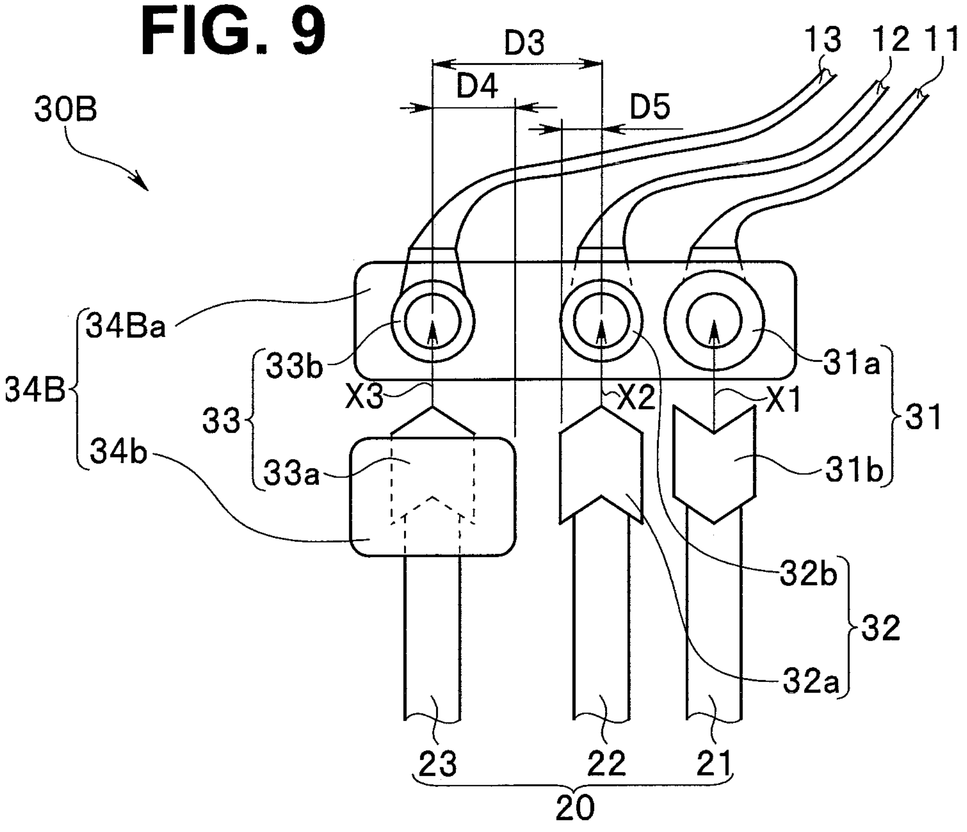
FIG. 9 is a schematic diagram illustrating correct connection combination of conduit connectors (before connection) in the insertion-instrument conduit connection device according to the second embodiment of the present disclosure.

An insertion-instrument conduit connection device according to a second embodiment of the present disclosure will be described below with reference to FIGS. 8 and 9. FIG. 8 is a schematic configuration diagram illustrating the insertion-instrument conduit connection device according to the second embodiment of the present disclosure in an enlarging manner. FIG. 9 is a schematic diagram illustrating correct connection combination of the conduit connectors (31, 32, and 33) of the insertion-instrument conduit connection device according to the present embodiment (before connection).

The insertion-instrument conduit connection device according to the second embodiment of the present disclosure has substantially the same basic configuration as in the first embodiment described above. In the present embodiment, the fixation member of each interference component has a slightly different configuration. Thus, among components in the present embodiment, any component same as in the first embodiment described above is denoted by the same reference sign, and description thereof is omitted. Any component different from a component in the first embodiment described above will be described below.

In an insertion-instrument conduit connection device 30B according to the present embodiment, each interference component 34B is constituted by a fixation member 34Ba and the interference member 34*b* as illustrated in FIGS. 8 and 9.

The fixation member 34Ba adjacently holds and fixes the connection body 31*a* of the first conduit connector 31, the connection counterpart body 32*b* of the second conduit connector 32, and the connection counterpart body 33*b* of the third conduit connector 33 in parallel. Thus, the fixation member 34Ba is provided with a plurality of holes 34Bax that allow insertion of the first fluid circulation conduit (11 and 21), the second fluid circulation conduit (12 and 22), and the third fluid circulation conduit (13 and 23) or insertion of the first conduit connector 31, the second conduit connector 32, and the third conduit connector 33.

In this case, an interval is provided between the first conduit connector 31 (connection body 31*a*) or the second conduit connector 32 (connection counterpart body 32*b*) fixed by the fixation member 34Ba and the third conduit connector 33 (connection counterpart body 33*b*), the interval having a size with which connection by the interference member 34*b* is not interrupted.

A reference sign D3 illustrated in FIG. 9 represents a center interval between the second conduit connector 32 (connection counterpart body 32*b*) fixed by the fixation member 34Ba and the third conduit connector 33 (connection counterpart body 33*b*). A reference sign D4 illustrated in FIG. 9 represents a distance in a radial direction from a central axis of the interference member 34*b* provided at the connection body 33*a* of the third conduit connector 33 to an outer shape line. A reference sign D5 illustrated in FIG. 9 represents a distance in a radial direction from a central axis of the connection body 32*a* of the second conduit connector to an outer shape line.

In this case, the interval D3 in a size with which connection by the interference member 34*b* is not interrupted is set to satisfy $$D3>D4+D5.$$

The other configuration is the same as in the first embodiment described above.

In the above-described second embodiment thus configured, as well, it is possible to obtain substantially the same workings and effects as in the first embodiment described above.

Moreover, in the configuration according to the present embodiment, the plurality (three) of conduit connectors (31, 32, and 33) are fixed and held by using one fixation member 34Ba. With such a configuration, the plurality of conduit connectors can be collectively managed in the present embodiment, and thus wrong connection can be prevented and connection work can be easily and efficiently performed.

Note that the configuration exemplarily described in the modification of the first embodiment described above can be applied substantially in the same manner in the present embodiment as well.

Specifically, although not illustrated, when the fixation member 34Ba is provided with the same grooves (grooves extending from an outer surface to the holes 34Bax) as the grooves illustrated in FIG. 7, the connection body 31*a* of the first conduit connector 31, the connection counterpart body 32*b* of the second conduit connector 32, and the connection counterpart body 33*b* of the third conduit connector 33 can be easily disposed, held, and fixed in the holes 34Bax of the fixation member 34Ba. In this case as well, it is possible to obtain substantially the same workings and effects as in the modification of the first embodiment described above.

An insertion-instrument conduit connection device according to a third embodiment of the present disclosure will be described below with reference to FIGS. 10 to 12.

Figure 10:
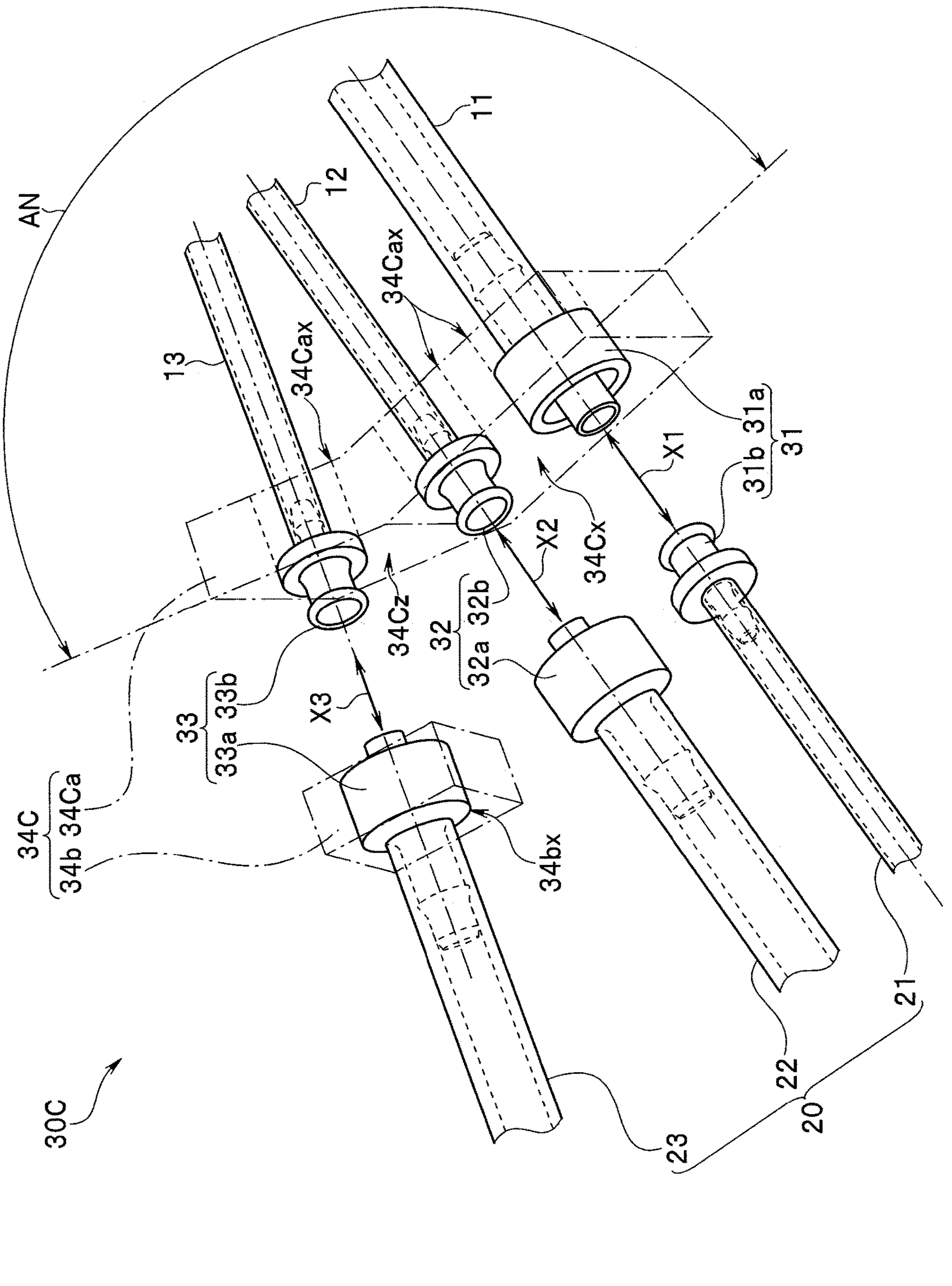
FIG. 10 is a schematic configuration diagram illustrating an insertion-instrument conduit connection device according to a third embodiment of the present disclosure in an enlarging manner.

FIG. 10 is a schematic configuration diagram illustrating the insertion-instrument conduit connection device according to the third embodiment of the present disclosure in an enlarging manner. FIGS. 11 and 12 are each a schematic diagram for description of workings of the insertion-instrument conduit connection device according to the present embodiment. FIG. 11 illustrates correct connection combination of the conduit connectors (31, 32, and 33) of the insertion-instrument conduit connection device before connection. FIG. 12 illustrates an example of wrong connection combination of the conduit connectors (31, 32, and 33) of the insertion-instrument conduit connection device.

The insertion-instrument conduit connection device according to the present embodiment has substantially the same basic configuration as in the second embodiment described above. In the present embodiment, the fixation member of each interference component has a slightly different configuration. Thus, among components in the present embodiment, any component same as in the second embodiment described above is denoted by the same reference sign, and description thereof is omitted. Any component different from a component in the second embodiment described above will be described below.

In an insertion-instrument conduit connection device 30C according to the present embodiment, each interference component 34C is constituted by a fixation member 34Ca and the interference member 34*b* as illustrated in FIG. 10. The fixation member 34Ca is provided with a plurality of holes 34Cax that allow insertion of the first fluid circulation conduit (11 and 21), the second fluid circulation conduit (12 and 22), and the third fluid circulation conduit (13 and 23) or insertion of the first conduit connector 31, the second conduit connector 32, and the third conduit connector 33.

The fixation member 34Ca has substantially the same configuration as in the first embodiment described above with which the connection body 31*a* of the first conduit connector 31, the connection counterpart body 32*b* of the second conduit connector 32, and the connection counterpart body 33*b* of the third conduit connector 33 are adjacently held and fixed substantially in parallel.

In this case, the fixation member 34Ca according to the present embodiment has an angle AN between a first fixation surface 34Cx as a part that fixes the first conduit connector 31 or the second conduit connector 32 and a second fixation surface 34Cz as a part that fixes the third conduit connector 33, the angle AN having a size with which connection by the interference member 34*b* is not interrupted. The other configuration is the same as in the first embodiment described above.

Figure 11:
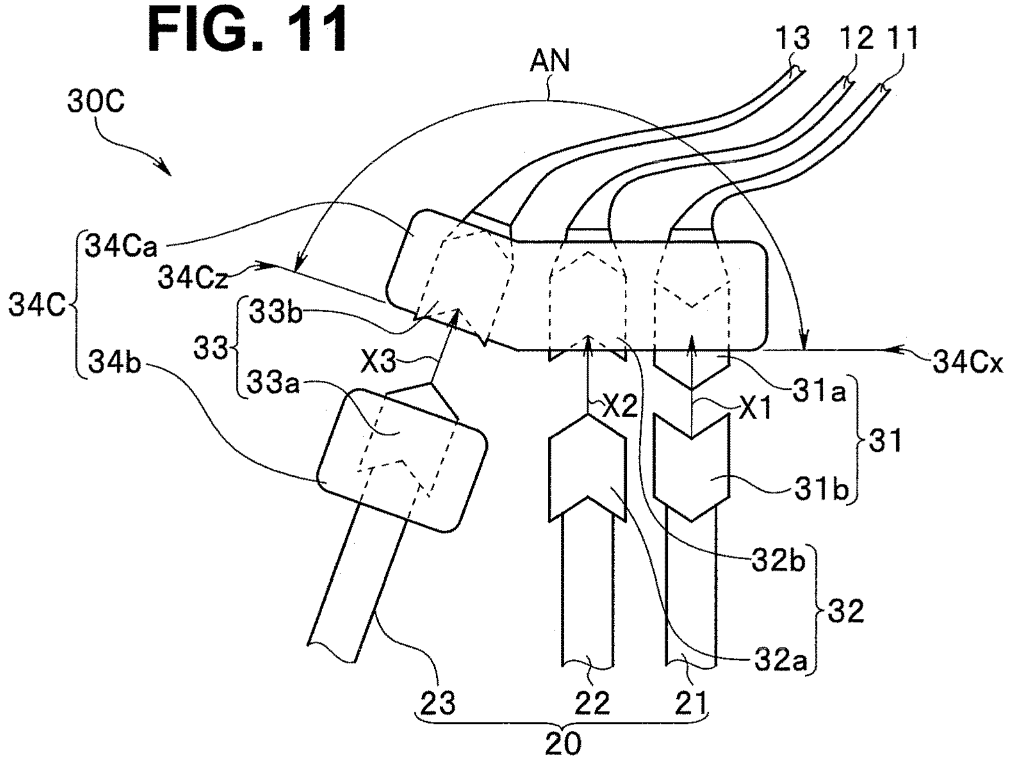
FIG. 11 is a schematic diagram for description of workings of the insertion-instrument conduit connection device according to the third embodiment of the present disclosure, illustrating correct connection combination of conduit connectors of the insertion-instrument conduit connection device (before connection).

In the above-described third embodiment thus configured, when the conduit connectors (31, 32, and 33) are connected in correct connection combination as illustrated in FIG. 11, for example, all connectors can be reliably connected without interference.

Figure 12:
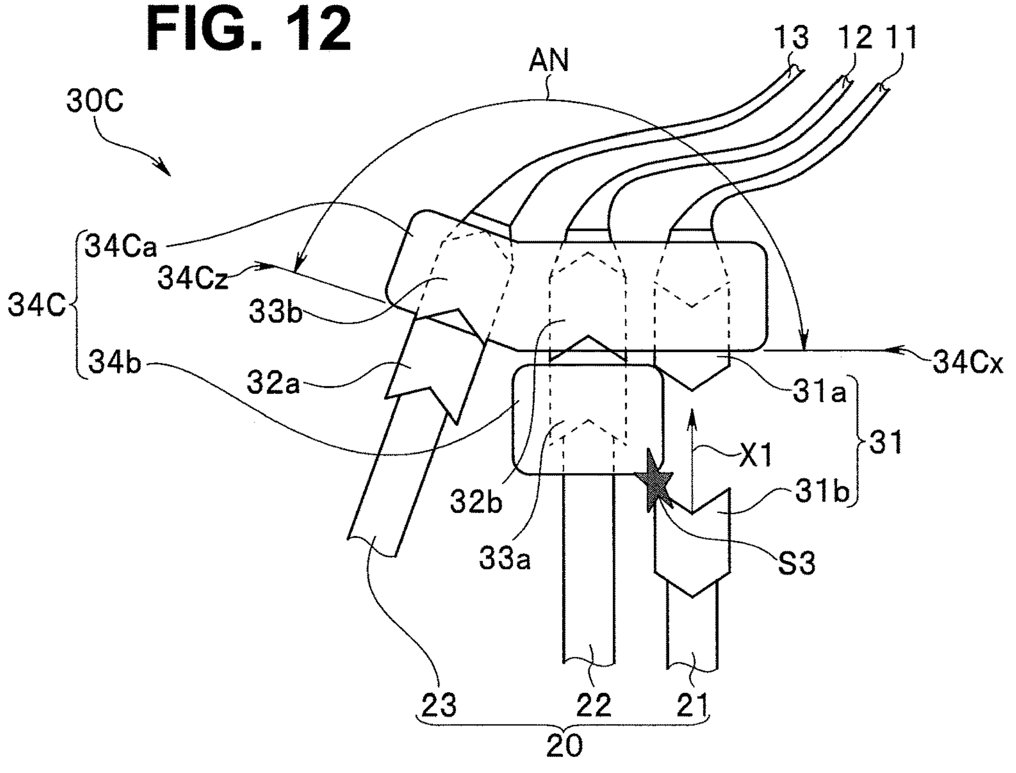
FIG. 12 is a schematic diagram for description of workings of the insertion-instrument conduit connection device according to the third embodiment of the present disclosure, illustrating an example of wrong connection combination of the conduit connectors of the insertion-instrument conduit connection device.

However, when the connection body 33*a* of the third conduit connector 33 is wrongly connected to the connection counterpart body 32*b* of the second conduit connector 32 as illustrated in FIG. 12, the connection counterpart body 31*b* interferes with the interference member 34*b* at a position indicated by a reference sign S3 in FIG. 12 as connection of the connection counterpart body 31*b* to the connection body 31*a* of the first conduit connector 31 is attempted in the arrow X1 direction in FIG. 12. Accordingly, connection between the connection body 31*a* and the connection counterpart body 31*b* is interrupted. Thus, the user can recognize wrong connection.

In this manner, in the present embodiment as well, it is possible to obtain substantially the same workings and effects as in the second embodiment described above.

An insertion-instrument conduit connection device according to a fourth embodiment of the present disclosure will be described below with reference to FIGS. 13 to 15.

Figure 13:
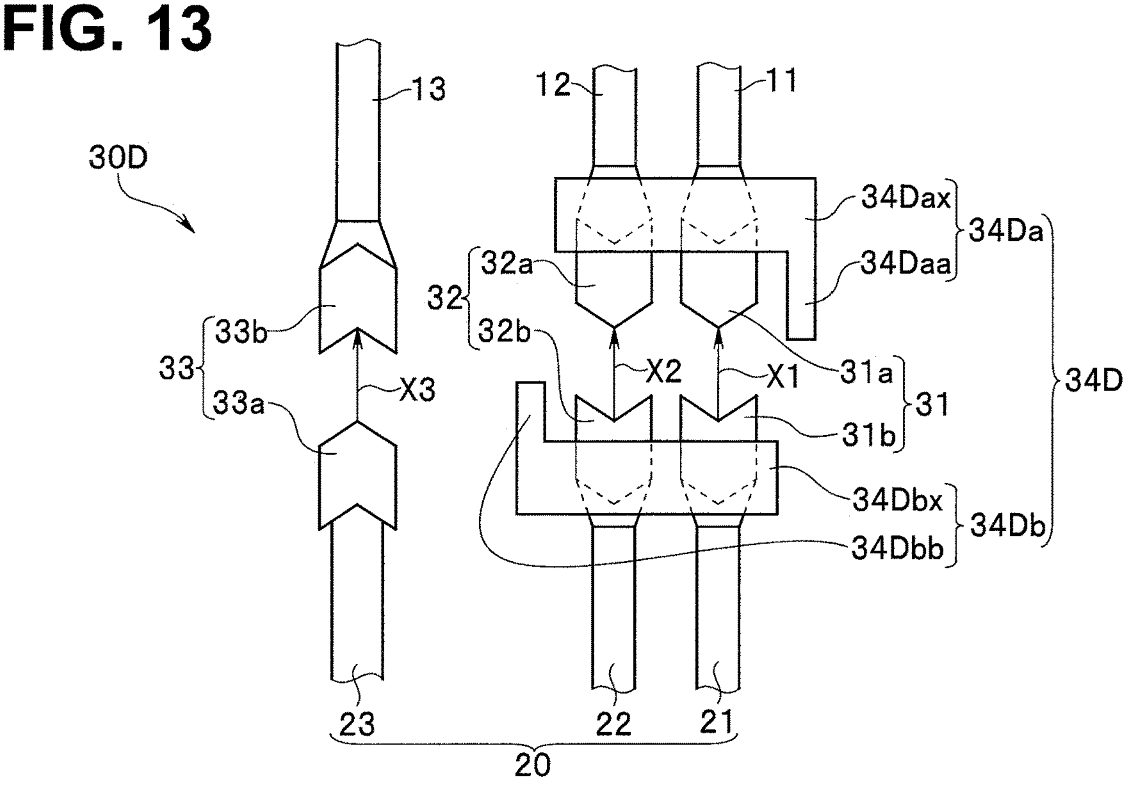
FIG. 13 is a schematic diagram illustrating an insertion-instrument conduit connection device according to a fourth embodiment of the present disclosure, illustrating correct connection combination of conduit connectors (before connection).
Figure 14:
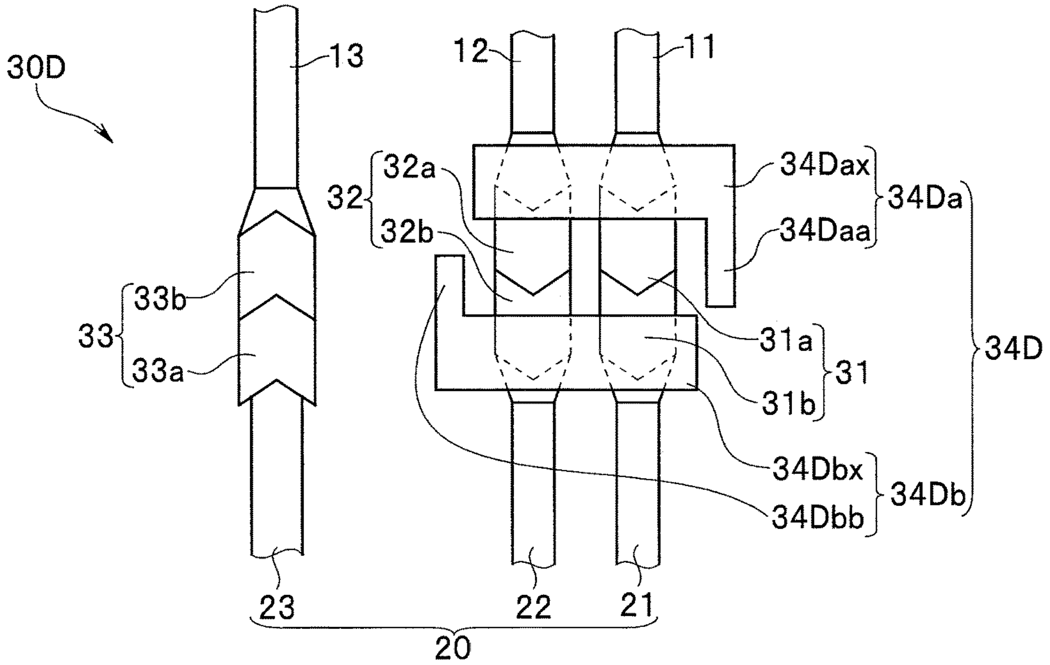
FIG. 14 is a schematic diagram illustrating the insertion-instrument conduit connection device according to the fourth embodiment of the present disclosure, illustrating correct connection combination of the conduit connectors (when connected).
Figure 15:
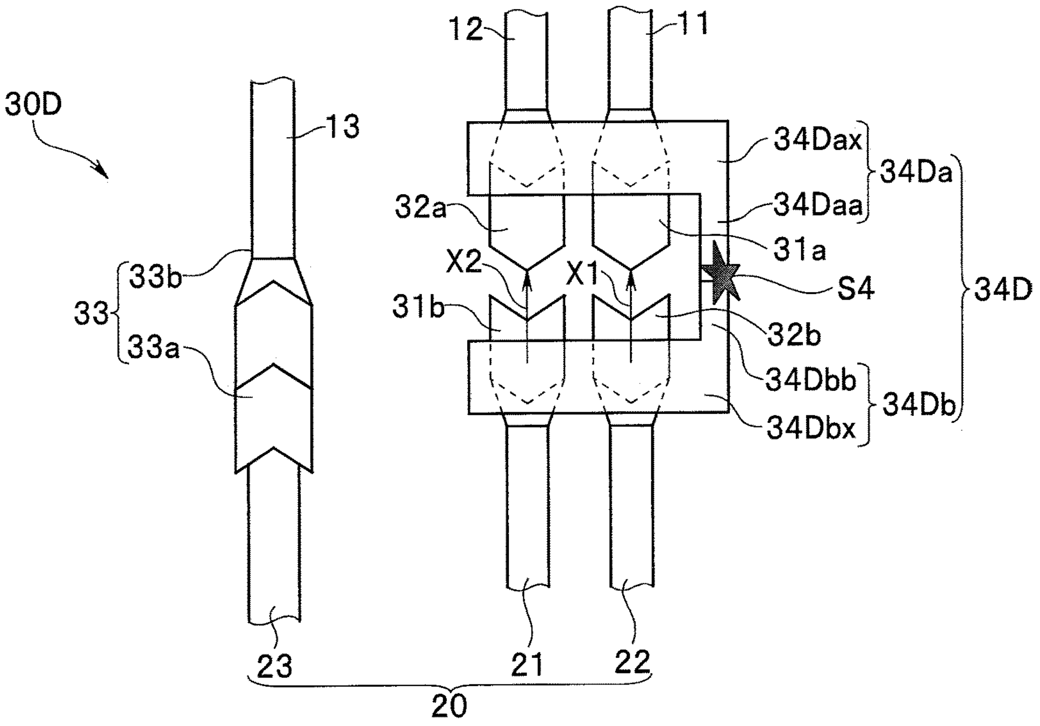
FIG. 15 is a schematic diagram illustrating the insertion-instrument conduit connection device according to the fourth embodiment of the present disclosure, illustrating wrong connection combination of the conduit connector.

FIGS. 13 to 15 are schematic diagrams illustrating the insertion-instrument conduit connection device according to the fourth embodiment of the present disclosure. FIGS. 13 and 14 illustrates correct connection combination of the conduit connectors (31, 32, and 33) of the insertion-instrument conduit connection device. FIG. 13 illustrates a state before connection. FIG. 14 illustrates a connected state. FIG. 15 illustrates wrong connection combination of the conduit connectors (31, 32, and 33) of the insertion-instrument conduit connection device.

The insertion-instrument conduit connection device according to the present embodiment has substantially the same basic configuration as in the first embodiment described above. In the present embodiment, each interference component has a slightly different configuration. Thus, among components in the present embodiment, any component same as in the first embodiment described above is denoted by the same reference sign, and description thereof is omitted. Any component different from a component in the first embodiment described above will be described below.

In an insertion-instrument conduit connection device 30D according to the present embodiment, each interference component 34D is constituted by a fixation member 34Da and an interference member 34Db as illustrated in FIG. 13.

The fixation member 34Da includes a fixation part 34Dax and a protrusion part 34Daa. The fixation part 34Dax is a constituent component that adjacently holds and fixes the connection body 31*a* of the first conduit connector 31 and the connection body 32*a* of the second conduit connector 32 in parallel. The protrusion part 34Daa is a constituent component formed as a protrusion extending outward in an orthogonal direction from a fixation surface that fixes the connection bodies (31*a* and 32*a*) of the first and second conduit connectors (31 and 32).

The interference member 34Db includes a fixation part 34Dbx and a protrusion part 34Dbb. The fixation part 34Dbx is a constituent component that adjacently holds and fixes the connection counterpart body 31*b* of the first conduit connector 31 and the connection counterpart body 32*b* of the second conduit connector 32 in parallel. The protrusion part 34Dbb is a constituent component formed as a protrusion extending outward in an orthogonal direction from a fixation surface that fixes the connection counterpart bodies (31*b* and 32*b*) of the first and second conduit connectors (31 and 32).

The protrusion part 34Dbb is a constituent component that does not interfere with the first and second conduit connectors in correct connection combination (refer to FIG. 14) but collides with part (the protrusion part 34Daa) of the fixation member 34Da to interrupt connection of the connectors in wrong connection combination (refer to FIG. 15) as described later.

In the present embodiment, among the plurality of fluid circulation conduits, the first conduit connector 31 provided at the first fluid circulation conduit (11 and 21) and the second conduit connector 32 provided at the second fluid circulation conduit (12 and 22) have the same orientation or the same configuration.

Specifically, as illustrated, in the first fluid circulation conduit (11 and 21), the connection body 31*a* is provided at the water feeding conduit 11 and the connection counterpart body 31*b* is provided at the first relay conduit 21. In the second fluid circulation conduit (12 and 22), the connection body 32*a* is provided at the suction conduit 12 and the connection counterpart body 32*b* is provided at the second relay conduit 22.

In the present embodiment, the third conduit connector 33 provided at the third fluid circulation conduit (13 and 23) among the plurality of fluid circulation conduits has orientations different from or configurations different from the first and second conduit connectors (31 and 32).

Specifically, as illustrated, in the third fluid circulation conduit (13 and 33), the connection counterpart body 33*b* is provided at the suction clogging resolution conduit 13 and the connection body 33*a* is provided at the third relay conduit 23.

In the above-described fourth embodiment thus configured, when the conduit connectors (31, 32, and 33) are connected in correct connection combination as illustrated in FIGS. 13 and 14, for example, all connectors can be reliably connected without interference.

However, when the connection counterpart body 32*b* of the second conduit connector 32 is disposed oppositely to the connection body 31*a* of the first conduit connector 31, the connection counterpart body 31*b* of the first conduit connector 31 is disposed oppositely to the connection body 32*a* of the second conduit connector 32, and connection is attempted in the arrow X1 and X2 directions in FIG. 15 as illustrated in FIG. 15, the protrusion part 34Dbb of the interference member 34Db and the protrusion part 34Daa as part of the fixation member 34Da collide with each other at a position indicated by a reference sign S4 in FIG. 15 before the connectors are connected to each other. Accordingly, connection between the connection body 31*a* and the connection counterpart body 32*b* and connection between the connection body 32*a* and the connection counterpart body 31*b* are interrupted. Thus, the user can recognize wrong connection.

In the above-described fourth embodiment thus configured, as well, it is possible to obtain substantially the same actions and workings as in each above-described embodiment.

Note that although a configuration example in which the plurality of fluid circulation conduits include three fluid circulation conduits is described above in the fourth embodiment, the plurality of fluid circulation conduits are not limited to the above-described configuration example. For example, the third fluid circulation conduit (23 and 13) may be removed from the configuration example in the fourth embodiment described above and at least the first and second fluid circulation conduits (21 and 11, and 22 and 12) may be provided.

An insertion-instrument conduit connection device according to a fifth embodiment of the present disclosure will be described below with reference to FIGS. 16 and 17.

Figure 16:
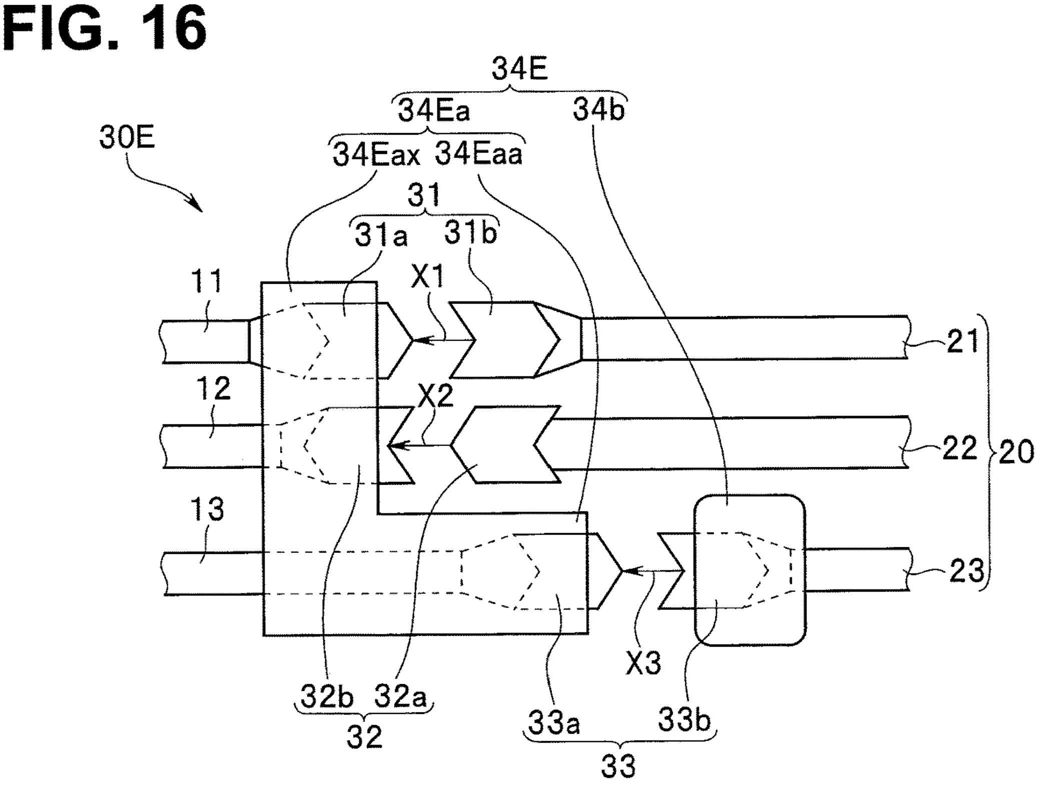
FIG. 16 is a schematic diagram illustrating an insertion-instrument conduit connection device according to a fifth embodiment of the present disclosure, illustrating correct connection combination of conduit connectors.
Figure 17:
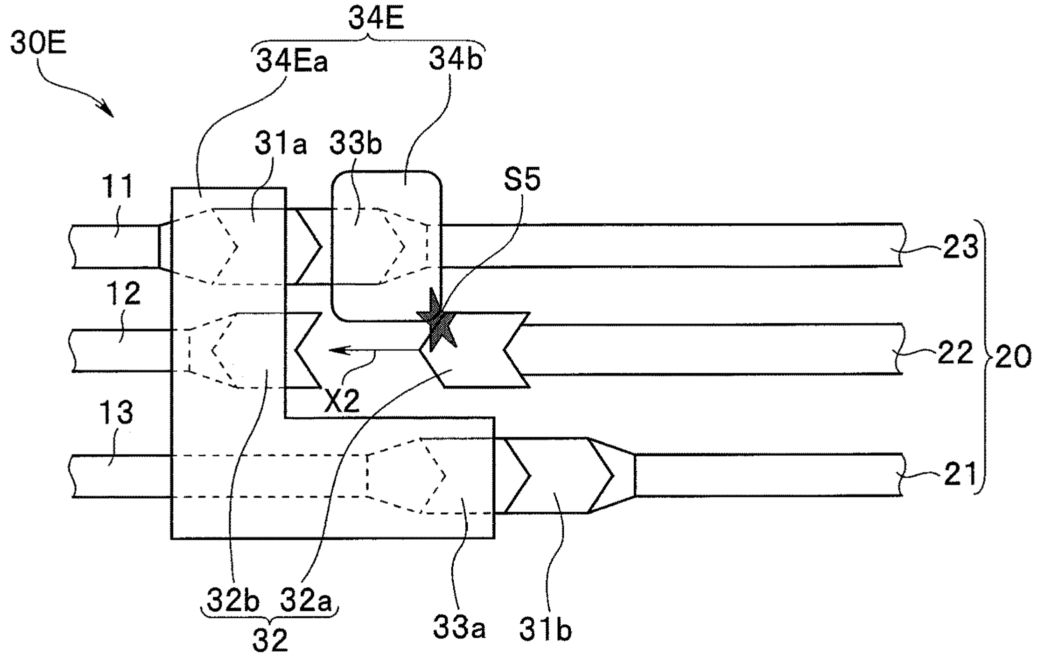
FIG. 17 is a schematic diagram illustrating wrong connection combination of the conduit connectors in the insertion-instrument conduit connection device in FIG. 16.

FIGS. 16 and 17 are schematic diagrams illustrating the insertion-instrument conduit connection device according to the fifth embodiment of the present disclosure. FIG. 16 illustrates correct connection combination of the conduit connectors (31, 32, and 33) of the insertion-instrument conduit connection device (before connection). FIG. 17 illustrates wrong connection combination of the conduit connectors (31, 32, and 33) of the insertion-instrument conduit connection device.

The insertion-instrument conduit connection device according to the present embodiment has substantially the same basic configuration as in the first embodiment described above. In the present embodiment, each interference component has a slightly different configuration. Thus, among components in the present embodiment, any component same as in, for example, the first embodiment described above is denoted by the same reference sign, and description thereof is omitted. Any component different from a component in, for example, the first embodiment described above will be described below.

In an insertion-instrument conduit connection device 30E according to the present embodiment, each interference component 34E is constituted by a fixation member 34Ea and the interference member 34*b* as illustrated in FIGS. 16 and 17.

The fixation member 34Ea includes a fixation part 34Eax and a protrusion part 34Eaa. The fixation part 34Eax adjacently holds and fixes the connection body 31*a* of the first conduit connector 31 (the end of the water feeding conduit 11) and the connection counterpart body 32*b* of the second conduit connector 32 (the end of the suction conduit 12) in parallel to the long axis direction.

The protrusion part 34Eaa is formed as a protrusion extending outward in an orthogonal direction from a fixation surface that fixes the connection body 31*a* and the connection counterpart body 32*b*. The connection body 33*a* of the third conduit connector 33 (the end of the suction clogging resolution conduit 13) is held and fixed at a tip part of the protrusion part 34Eaa.

In such a configuration of the fixation member 34Ea, the connection body 33*a* is adjacently disposed in parallel to the connection body 31*a* and the connection counterpart body 32*b* when viewed in the long axis direction. The connection body 33*a* is also disposed at a position different from the positions of the connection body 31*a* and the connection counterpart body 32*b* in the long axis direction.

The interference member 34*b* is provided at the connection counterpart body 33*b* at the one end of the third relay conduit 23. Note that an interference member having the same form as the interference member 34*b* described above in the first embodiment is applied as the interference member 34*b*.

In the present embodiment, the first conduit connector 31 provided at the first fluid circulation conduit (11 and 21) and the third conduit connector 33 provided at the third fluid circulation conduit (13 and 23) among the plurality of fluid circulation conduits have the same orientation or the same configuration.

Specifically, as illustrated in FIG. 16, in the first fluid circulation conduit (11 and 21), the connection body 31*a* is provided at the water feeding conduit 11 and the connection counterpart body 31*b* is provided at the first relay conduit 21. In the third fluid circulation conduit (13 and 23), the connection body 33*a* is provided at the suction clogging resolution conduit 13 and the connection counterpart body 33*b* is provided at the third relay conduit 23.

In the present embodiment, the second conduit connector 32 provided at the second fluid circulation conduit (12 and 22) among the plurality of fluid circulation conduits has orientations different from or configurations different from the first and third conduit connectors (31 and 33).

Specifically, as illustrated, in the second fluid circulation conduit (12 and 32), the connection counterpart body 32*b* is provided at the suction conduit 12 and the connection body 32*a* is provided at the second relay conduit 22.

In the above-described fifth embodiment thus configured, when the conduit connectors (31, 32, and 33) are connected in correct connection combination (refer to the arrows X1, X2, and X3) as illustrated in FIG. 16, for example, all connectors can be reliably connected without interference.

However, when the connection counterpart body 33*b* is connected to the connection body 31*a* and the connection counterpart body 31*b* is connected to the connection body 33*a* as illustrated in FIG. 17, the interference member 34*b* and the connection body 32*a* collide with each other at a position indicated by a reference sign S5 in FIG. 17 as connection of the connection body 32*a* to the connection counterpart body 32*b* of the second conduit connector 32 is attempted (refer to the arrow X2 in FIG. 17). Accordingly, connection between the connection counterpart body 32*b* and the connection body 32*a* is interrupted. Thus, the user can recognize wrong connection.

In the configuration according to the present embodiment, although not illustrated, when connection of the connection counterpart body 33*b* to the connection body 31*a* is attempted while the connection body 32*a* is connected to the connection counterpart body 32*b*, as well, the connection body 32*a* and the interference member 34*b* collide with each other and connection between the connection body 31*a* and the connection counterpart body 33*b* is interrupted. Thus, the user can recognize wrong connection.

In the above-described fifth embodiment thus configured, as well, it is possible to obtain substantially the same workings and effects as in each above-described embodiment.

Figure 18:
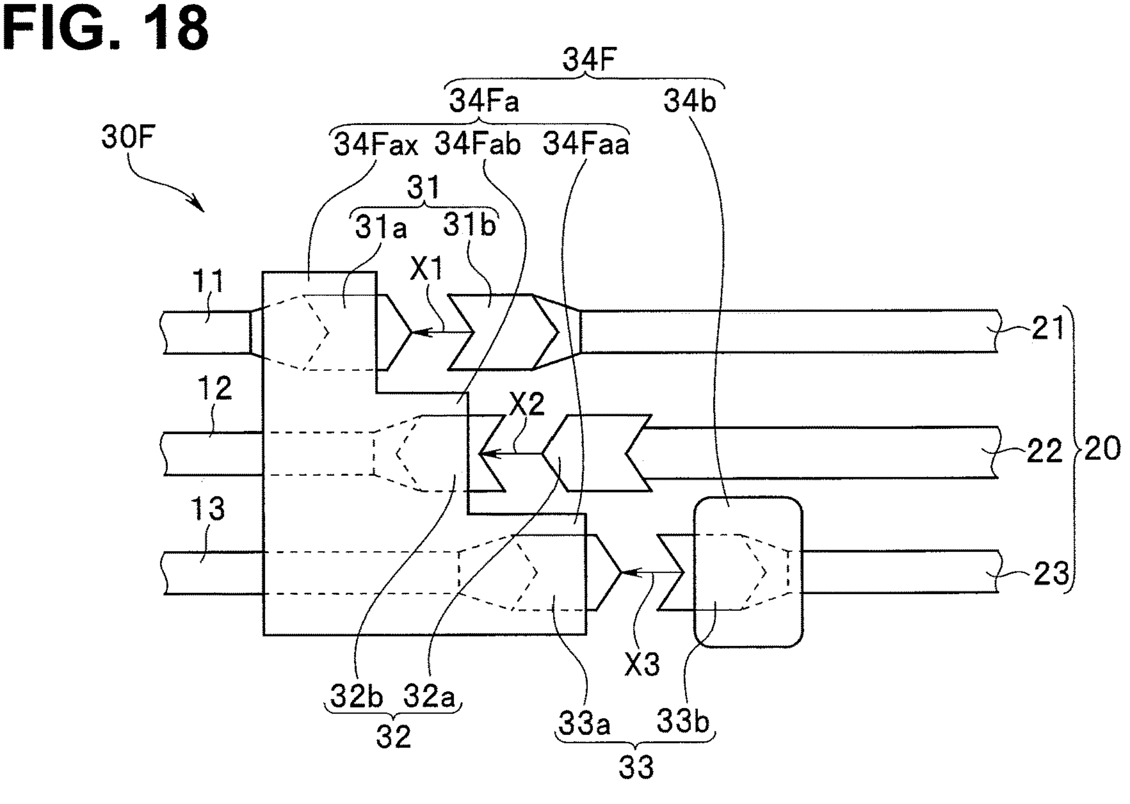
FIG. 18 is a schematic diagram illustrating an insertion-instrument conduit connection device according to a first modification of the fifth embodiment of the present disclosure, illustrating correct connection combination of conduit connectors.
Figure 19:
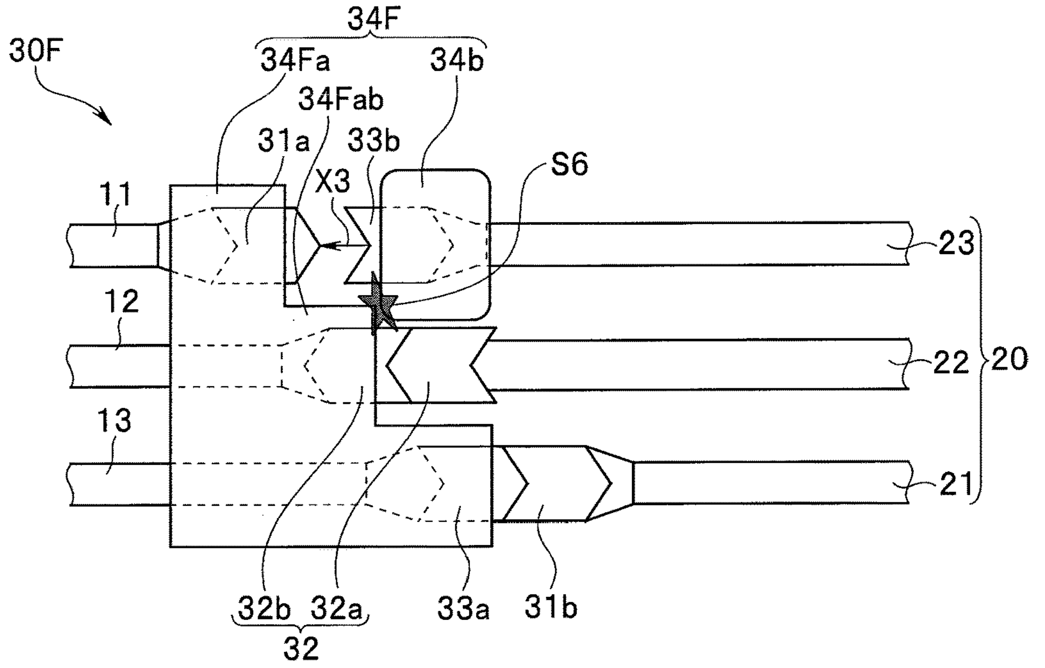
FIG. 19 is a schematic diagram illustrating wrong connection combination of the conduit connectors in the insertion-instrument conduit connection device in FIG. 18.

Modifications of the fifth embodiment described above will be described below. FIGS. 18 and 19 are schematic diagrams illustrating an insertion-instrument conduit connection device according to a first modification of the fifth embodiment of the present disclosure. FIG. 18 illustrates correct connection combination of the conduit connectors (31, 32, and 33) of the insertion-instrument conduit connection device (before connection). FIG. 19 illustrates wrong connection combination of the conduit connectors (31, 32, and 33) of the insertion-instrument conduit connection device.

The insertion-instrument conduit connection device according to the present modification has substantially the same basic configuration as in the fifth embodiment described above. In the present modification, each interference component has a slightly different configuration. Specifically, each interference component 34F in an insertion-instrument conduit connection device 30F according to the present modification is constituted by a fixation member 34Fa and the interference member 34*b* as illustrated in FIGS. 18 and 19.

The fixation member 34Fa holds and fixes the first conduit connector 31, the second conduit connector 32, and the third conduit connector 33 in parallel when viewed in the long axis direction. In this case, the fixation member 34Fa disposes, at different positions in the long axis direction, the conduit connectors (31, 32, and 33) of the water feeding conduit 11, the suction conduit 12, the suction clogging resolution conduit 13, respectively, or of the conduits (21, 22, and 23) of the relay fluid circulation conduits 20, respectively. With such a configuration, wrong connection of the conduit connectors (31, 32, and 33) is prevented.

Specifically, the fixation member 34Fa includes a fixation part 34Fax, a second protrusion part 34Fab, and a first protrusion part 34Faa. The fixation part 34Fax holds and fixes the connection body 31*a* of the first conduit connector 31 (the end of the water feeding conduit 11).

The second protrusion part 34Fab is formed as a protrusion extending outward by a predetermined amount in an orthogonal direction from a fixation surface of the fixation part 34Fax at which the connection body 31*a* is fixed. The second protrusion part 34Fab holds and fixes the connection counterpart body 32*b* of the second conduit connector 32 (the end of the suction conduit 12). Accordingly, the connection counterpart body 32*b* is disposed at a position shifted by the predetermined amount in the long axis direction from a position at which the connection body 31*a* is disposed.

The first protrusion part 34Faa is formed as a protrusion extending outward by a predetermined amount in an orthogonal direction from a fixation surface of the second protrusion part 34Fab at which the connection counterpart body 32*b* is fixed. The first protrusion part 34Faa holds and fixes the connection body 33*a* of the third conduit connector 33 (the end of the suction clogging resolution conduit 13). Accordingly, the connection body 33*a* is disposed at a position shifted by the predetermined amount in the long axis direction from a position at which the connection counterpart body 32*b* is disposed.

In this manner, the fixation part 34Fax, the second protrusion part 34Fab, and the first protrusion part 34Faa of the fixation member 34Fa are disposed in parallel at adjacent positions when viewed in the long axis direction. Simultaneously, the fixation part 34Fax, the second protrusion part 34Fab, and the first protrusion part 34Faa are disposed at positions different from one another in the long axis direction.

Note that the orientation or configuration of each conduit connector provided at a fluid circulation conduit in the present modification is the same as in the fifth embodiment described above. The interference member 34*b* is provided at the connection counterpart body 33*b* of the third relay conduit 23. The other configuration is substantially the same as in the fifth embodiment described above.

In the above-described first modification of the fifth embodiment thus configured, when the conduit connectors (31, 32, and 33) are connected in correct connection combination (refer to the arrows X1, X2, and X3) as illustrated in FIG. 18, all connectors can be reliably connected without interference.

Connection between the connection counterpart body 32*b* of the second conduit connector 32 and the connection body 32*a* and connection between the connection body 33*a* and the connection counterpart body 31*b* can be ensured as illustrated in FIG. 19. However, the interference member 34*b* collides with part (the second protrusion part 34Fab) of the fixation member 34Fa at a position indicated by a reference sign S6 in FIG. 19 as connection of the connection counterpart body 33*b* to the connection body 31*a* is attempted (refer to the arrow X3 in FIG. 19). Accordingly, the user can recognize the attempt for wrong connection.

According to the above-described first modification thus configured, it is possible to obtain substantially the same workings and effects as in the fifth embodiment described above.

Figure 20:
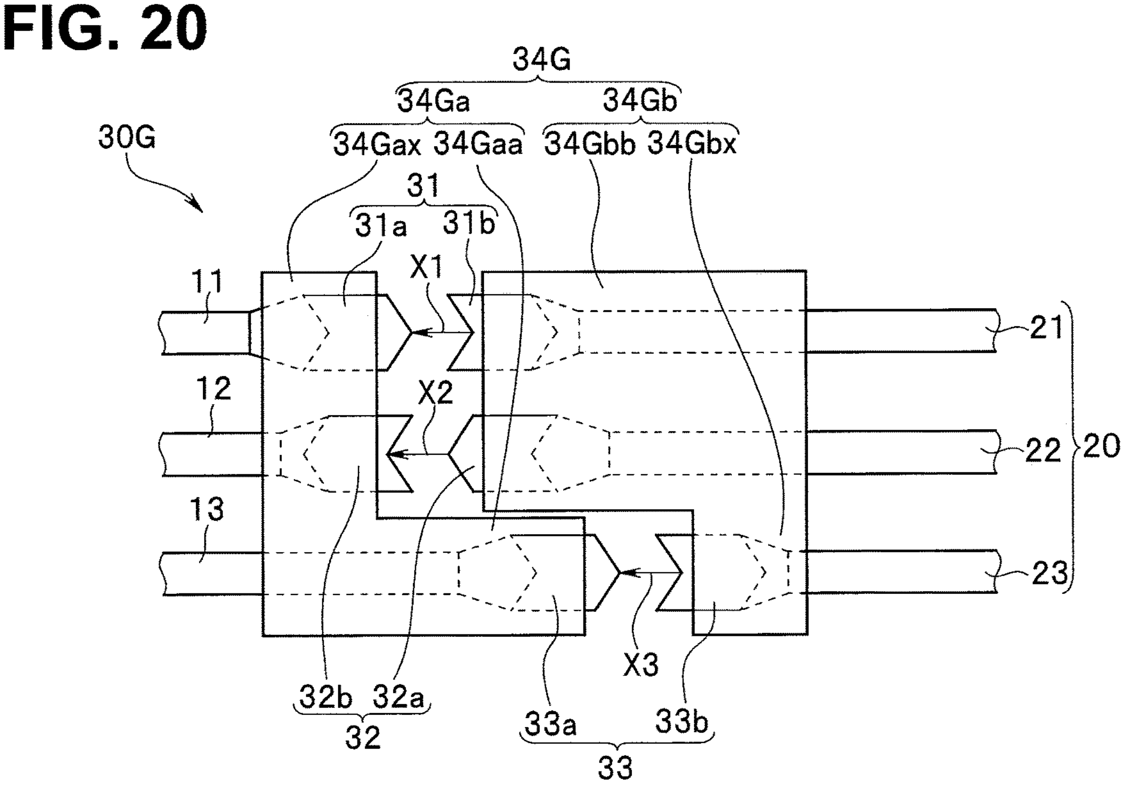
FIG. 20 is a schematic diagram illustrating an insertion-instrument conduit connection device according to a second modification of the fifth embodiment of the present disclosure, illustrating correct connection combination of conduit connectors.
Figure 21:
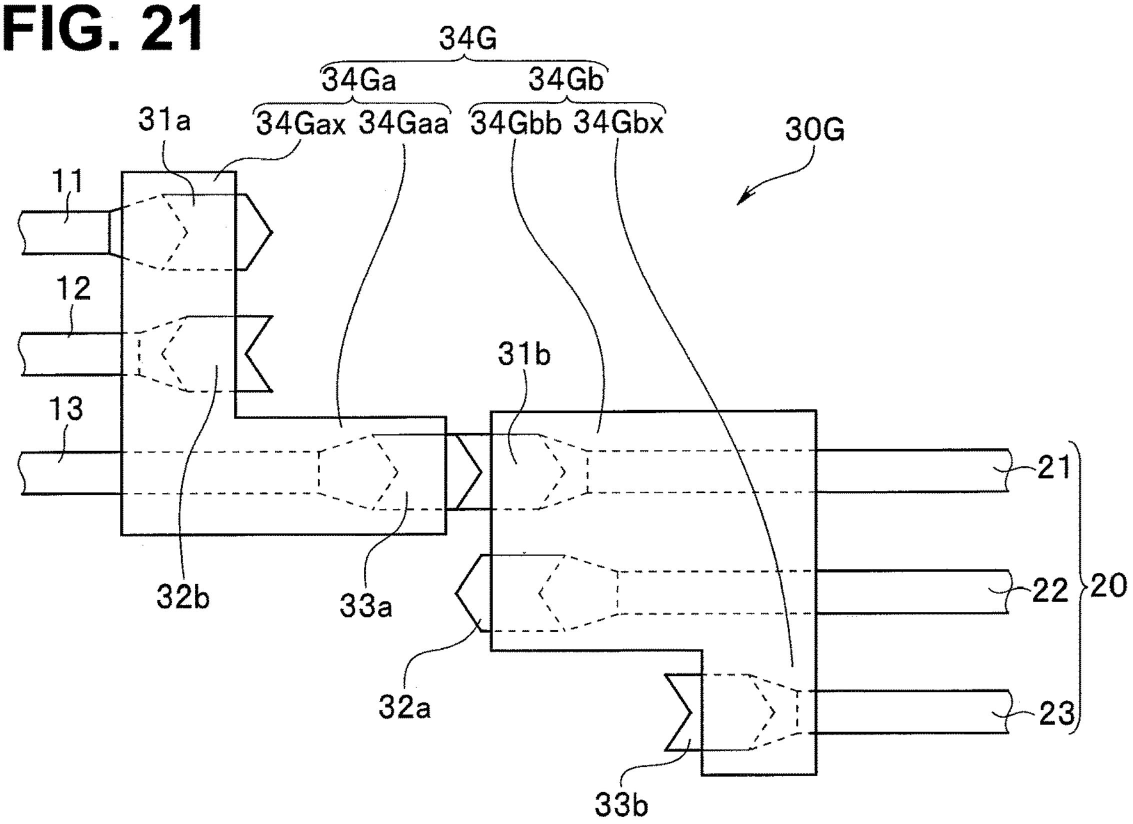
FIG. 21 is a schematic diagram illustrating a first example of wrong connection combination of the conduit connectors in the insertion-instrument conduit connection device in FIG. 20.
Figure 22:
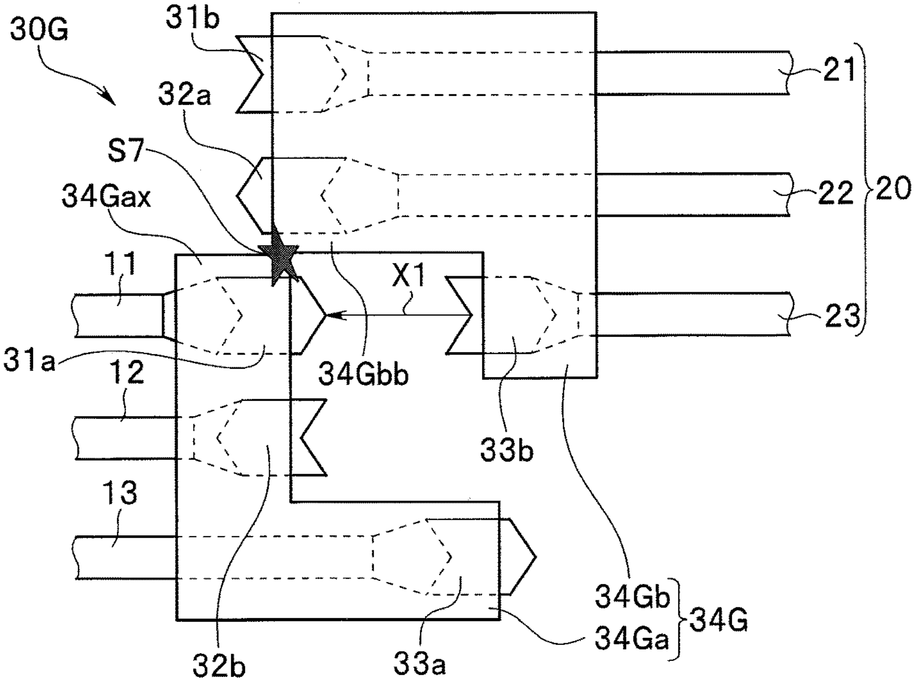
FIG. 22 is a schematic diagram illustrating a second example of wrong connection combination of the conduit connectors in the insertion-instrument conduit connection device in FIG. 20.

FIGS. 20 to 22 are schematic diagrams illustrating an insertion-instrument conduit connection device according to a second modification of the fifth embodiment of the present disclosure. FIG. 20 illustrates correct connection combination of the conduit connectors (31, 32, and 33) of the insertion-instrument conduit connection device (before connection). FIGS. 21 and 22 illustrate two examples of wrong connection combination of the conduit connectors (31, 32, and 33) of the insertion-instrument conduit connection device.

The insertion-instrument conduit connection device according to the present modification has substantially the same basic configuration as in the fifth embodiment described above. In the present modification, each interference component has a slightly different configuration. Specifically, each interference component 34G in an insertion-instrument conduit connection device 30G according to the present modification is constituted by a fixation member 34Ga and an interference member 34Gb as illustrated in FIGS. 20 to 22. The fixation member 34Ga has substantially the same configuration as the fixation member 34Ea of each interference component 34E in the fifth embodiment described above (refer to FIGS. 16 and 17).

In brief description, the fixation member 34Ga includes a fixation part 34Gax and a protrusion part 34Gaa. The fixation part 34Gax adjacently holds and fixes the connection body 31*a* of the first conduit connector 31 (the end of the water feeding conduit 11) and the connection counterpart body 32*b* of the second conduit connector 32 (the end of the suction conduit 12) in parallel to the long axis direction.

The protrusion part 34Gaa is formed as a protrusion extending outward in an orthogonal direction from a fixation surface of the fixation part 34Gax at which the connection body 31*a* and the connection counterpart body 32*b* are fixed. The protrusion part 34Eaa holds and fixes the connection body 33*a* (the end of the suction clogging resolution conduit 13) of the third conduit connector 33.

The interference member 34Gb is formed in a shape in accordance with a shape of the fixation member 34Ga. Thus, the interference member 34Gb includes a fixation part 34Gbx and a protrusion part 34Gbb. When the conduit connectors (31, 32, and 33) of the insertion-instrument conduit connection device 30G are correctly connected, the protrusion part 34Gbb of the interference member 34Gb is disposed oppositely to the fixation part 34Gax of the fixation member 34Ga and the fixation part 34Gbx of the interference member 34Gb is disposed oppositely to the protrusion part 34Gaa of the fixation member 34Ga.

The protrusion part 34Gbb of the interference member 34Gb adjacently holds and fixes the connection counterpart body 31*b* of the first conduit connector 31 (the one end of the first relay conduit 21) and the connection body 32*a* of the second conduit connector 32 (the one end of the second relay conduit 22) in parallel to the long axis direction.

The fixation part 34Gbx of the interference member 34Gb holds and fixes the connection counterpart body 33*b* (the one end of the third relay conduit 23) of the third conduit connector 33.

In this configuration, the connection counterpart body 33*b* is adjacently disposed in parallel to the connection counterpart body 31*b* and the connection body 32*a* when viewed in the long axis direction. The connection counterpart body 33*b* is also disposed at a position different from positions of the connection counterpart body 31*b* and the connection body 32*a* in the long axis direction. The other configuration is substantially the same as in the fifth embodiment described above.

In the above-described second modification of the fifth embodiment thus configured, when the conduit connectors (31, 32, and 33) are connected in correct connection combination as illustrated in FIG. 20 (refer to the arrows X1, X2, and X3), all connectors can be reliably connected without interference.

For example, when the connection counterpart body 31*b* is connected to the connection body 33*a* as illustrated in FIG. 21, connection positions are shifted between the connection body 31*a* and the connection counterpart body 32*b* on the fixation member 34Ga side and the connection body 32*a* and the connection counterpart body 33*b* on the interference member 34Gb side, and accordingly, correct connection of the conduit connectors (31, 32, and 33) is impossible. Thus, the user can recognize wrong connection.

For example, when connection of the connection counterpart body 33*b* to the connection body 31*a* is attempted as illustrated in FIG. 22 (refer to the arrow X1 in FIG. 22), the protrusion part 34Gbb of the interference member 34Gb collides with the fixation part 34Gax of the fixation member 34Ga at a position indicated by a reference sign S7 in FIG. 22. Accordingly, connection between the connection body 31*a* and the connection counterpart body 33*b* is interrupted.

Simultaneously in this case, connection positions are shifted between the connection counterpart body 32*b* and the connection body 33*a* on the fixation member 34Ga side and the connection counterpart body 31*b* and the connection body 32*a* on the interference member 34Gb side. Accordingly, in this state, correct connection of the conduit connectors (31, 32, and 33) is impossible. Thus, the user can recognize wrong connection.

According to the above-described second modification thus configured, it is possible to obtain substantially the same workings and effects as in the fifth embodiment described above.

In the insertion-instrument conduit connection device 30G according to the present modification, each interference component 34G is constituted by the fixation member 34Ga and the interference member 34Gb. The fixation member 34Ga fixes the connection body 31*a*, the connection counterpart body 32*b*, and the connection body 33*a* of the conduit connectors (31, 32, and 33) as an integration. The interference member 34Gb fixes the connection body 31*a*, the connection counterpart body 32*b*, and the connection body 33*a* of the conduit connectors (31, 32, and 33) as an integration. Accordingly, correct connection of the conduit connectors (31, 32, and 33) is ensured only when the fixation member 34Ga and the interference member 34Gb are connected in a correct form.

Figure 23:
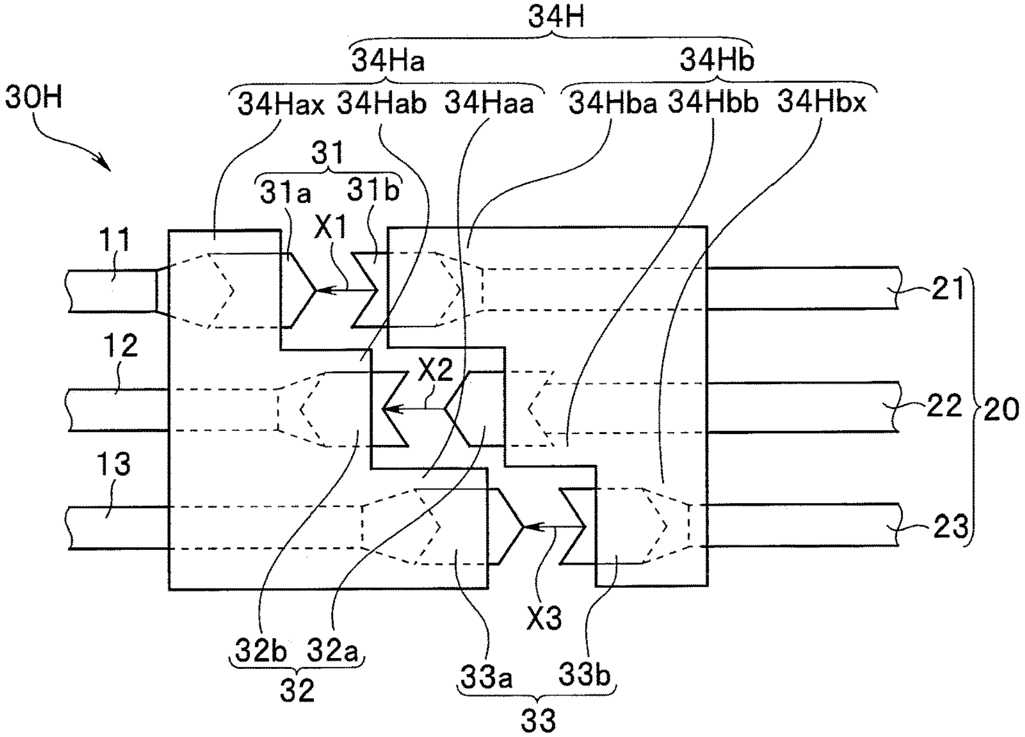
FIG. 23 is a schematic diagram illustrating an insertion-instrument conduit connection device according to a third modification of the fifth embodiment of the present disclosure, illustrating correct connection combination of conduit connectors.
Figure 24:
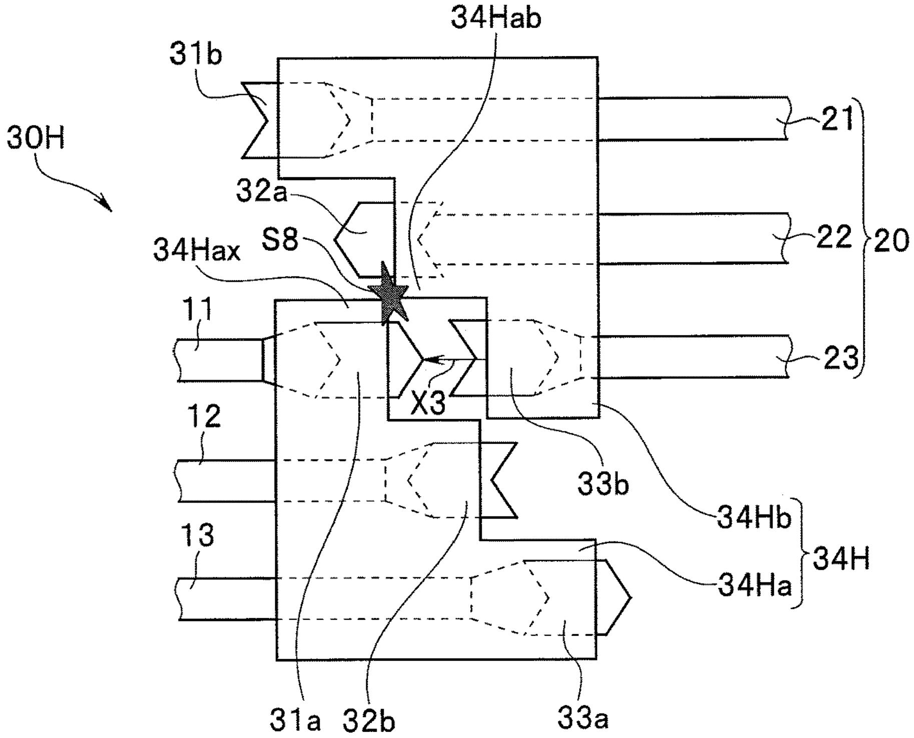
FIG. 24 is a schematic diagram illustrating wrong connection combination of the conduit connectors in the insertion-instrument conduit connection device in FIG. 23.

FIGS. 23 and 24 are schematic diagrams illustrating an insertion-instrument conduit connection device according to a third modification of the fifth embodiment of the present disclosure. FIG. 23 illustrates correct connection combination of the conduit connectors (31, 32, and 33) of the insertion-instrument conduit connection device (before connection). FIG. 24 illustrates wrong connection combination of the conduit connectors (31, 32, and 33) of the insertion-instrument conduit connection device.

The insertion-instrument conduit connection device according to the present modification has substantially the same basic configuration as in the above-described first modification. In the present modification, each interference component has a slightly different configuration. Specifically, each interference component 34H in an insertion-instrument conduit connection device 30H according to the present modification is constituted by a fixation member 34Ha and an interference member 34Hb as illustrated in FIGS. 23 and 24. The fixation member 34Ha has substantially the same configuration as the fixation member 34Fa of each interference component 34F in the above-described first modification (refer to FIGS. 18 and 19).

In brief description, the fixation member 34Ha includes a fixation part 34Hax, a second protrusion part 34Hab, and a first protrusion part 34Haa. The fixation part 34Hax holds and fixes the connection body 31*a* of the first conduit connector 31 (the end of the water feeding conduit 11).

The second protrusion part 34Hab is formed as a protrusion extending outward in an orthogonal direction from a fixation surface of the fixation part 34Hax at which the connection body 31*a* is fixed. The second protrusion part 34Hab holds and fixes the connection counterpart body 32*b* of the second conduit connector 32 (the end of the suction conduit 12). Accordingly, the connection counterpart body 32*b* is disposed at a position shifted by a predetermined amount in the long axis direction from a position at which the connection body 31*a* is disposed.

The first protrusion part 34Haa is formed as a protrusion extending outward in an orthogonal direction from a fixation surface of the second protrusion part 34Hab at which the connection counterpart body 32*b* is fixed. The first protrusion part 34Haa holds and fixes the connection body 33*a* of the third conduit connector 33 (the end of the suction clogging resolution conduit 13). Accordingly, the connection body 33*a* is disposed at a position shifted by a predetermined amount in the long axis direction from a position at which the connection counterpart body 32*b* is disposed.

In this manner, the fixation part 34Hax, the second protrusion part 34Hab, and the first protrusion part 34Haa of the fixation member 34Ha are disposed in parallel at adjacent positions when viewed in the long axis direction. The fixation part 34Hax, the second protrusion part 34Hab, and the first protrusion part 34Haa are also disposed at positions different from one another in the long axis direction.

The interference member 34Hb is formed in a shape in accordance with a shape of the fixation member 34Ha. Thus, the interference member 34Hb includes a fixation part 34Hbx, a second protrusion part 34Hbb, and a first protrusion part 34Hba. When the conduit connectors (31, 32, and 33) of the insertion-instrument conduit connection device 30H are correctly connected, the first protrusion part 34Hba of the interference member 34Hb is disposed oppositely to the fixation part 34Hax of the fixation member 34Ha. Similarly, the second protrusion part 34Hbb of the interference member 34Hb is disposed oppositely to the second protrusion part 34Hab of the fixation member 34Ha. Similarly, the fixation part 34Hbx of the interference member 34Hb is disposed oppositely to the first protrusion part 34Haa of the fixation member 34Ha.

The fixation part 34Hbx of the interference member 34Hb holds and fixes the connection counterpart body 33*b* (the one end of the third relay conduit 23) of the third conduit connector 33. The second protrusion part 34Hbb holds and fixes the connection body 32*a* (the one end of the second relay conduit 22) of the second conduit connector 32. The first protrusion part 34Hba holds and fixes the connection counterpart body 31*b* (the one end of the first relay conduit 21) of the first conduit connector 31.

In this configuration, the connection counterpart body 31*b*, the connection body 32*a*, and the connection counterpart body 33*b* are adjacently disposed in parallel when viewed in the long axis direction. The connection counterpart body 31*b*, the connection body 32*a*, and the connection counterpart body 33*b* are also disposed at different positions shifted from one another in the long axis direction. The other configuration is substantially the same as in the above-described first modification.

In the above-described third modification of the fifth embodiment thus configured, when the conduit connectors (31, 32, and 33) are connected in correct connection combination as illustrated in FIG. 23 (refer to the arrows X1, X2, and X3), all connectors can be reliably connected without interference.

For example, when connection of the connection counterpart body 33*b* to the connection body 31*a* is attempted as illustrated in FIG. 24 (refer to the arrow X3 in FIG. 24), the second protrusion part 34Hab of the interference member 34Hb collides with the fixation part 34Hax of the fixation member 34Ha at a position indicated by a reference sign S8 in FIG. 24. Accordingly, connection between the connection body 31*a* and the connection counterpart body 33*b* is interrupted.

Simultaneously in this case, connection positions are shifted between the connection counterpart body 32*b* and the connection body 33*a* on the fixation member 34Ha side and the connection counterpart body 31*b* and the connection body 32*a* on the interference member 34Hb side. Accordingly, in this state, correct connection of the conduit connectors (31, 32, and 33) is impossible. Thus, the user can recognize wrong connection.

According to the above-described third modification thus configured, it is possible to obtain substantially the same workings and effects as in the fifth embodiment described above.

Figure 25:
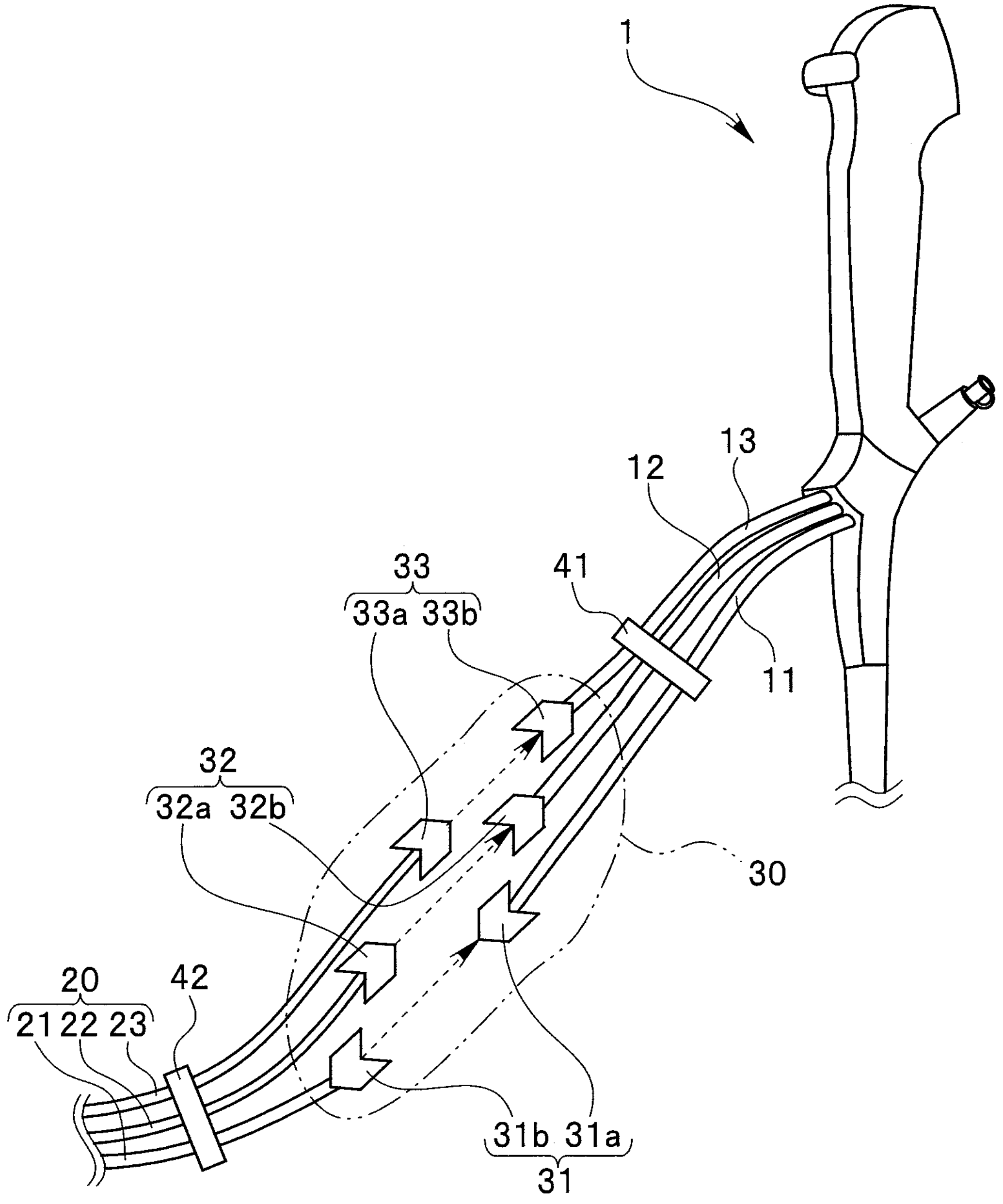
FIG. 25 is a schematic diagram illustrating an insertion-instrument conduit connection device according to a sixth embodiment of the present disclosure.

Note that, for example, a configuration as illustrated in FIG. 25 is applicable as the configuration in which the conduit connectors (31, 32, and 33) are disposed at different positions shifted from one another in the long axis direction as described above in the first and third modifications of the fifth embodiment. FIG. 25 is a schematic diagram illustrating an insertion-instrument conduit connection device of a sixth embodiment.

As illustrated in FIG. 25, in the insertion-instrument conduit connection device according to the sixth embodiment of the present disclosure, disposition of the conduit connectors (31, 32, and 33) in the long axis direction is set without providing an interference member.

In this configuration, the conduit connectors (31, 32, and 33) are disposed at positions shifted from one another in the long axis direction by adjusting respective lengths of the water feeding conduit 11, the suction conduit 12, the suction clogging resolution conduit 13, and the conduits (21, 22, and 23) of the relay fluid circulation conduits 20 in the long axis direction.

As illustrated in FIG. 25, the water feeding conduit 11, the suction conduit 12, and the suction clogging resolution conduit 13 are fixed at a predetermined halfway position by using a first binding member 41. Similarly, the conduits (21, 22, and 23) of the relay fluid circulation conduits 20 are fixed at a predetermined halfway position by using a second binding member 42. With this configuration, the connection body 31*a*, the connection counterpart body 32*b*, and the connection counterpart body 33*b* in the long axis direction are maintained at positions shifted from one another. Similarly, the connection counterpart body 31*b*, the connection body 32*a*, and the connection body 33*a* in the long axis direction are maintained at positions shifted from one another. With such a configuration as well, it is possible to obtain an effect of reducing wrong connection to some extent.

The present disclosure is not limited to the above-described embodiments but may be modified and applied in various kinds of manners without departing from the gist of the disclosure. Moreover, the above-described embodiments include disclosures at various kinds of stages, and various kinds of disclosures can be extracted by combining a plurality of disclosed components as appropriate. For example, when some components described in the above-described embodiments are deleted, a configuration in which the components are deleted can be extracted as an disclosure as long as the technical problem can be solved and the advantageous effects of the disclosure can be obtained. In addition, constituent components in different embodiments may be combined as appropriate. The present disclosure is limited by the accompanying claims but not constrained by a particular aspect.

1. An insertion-instrument conduit connection device comprising:
   - a plurality of conduit connectors attached to respective relay parts of a plurality of fluid circulation conduits connecting an insertion instrument and an external fluid circulation device; and
   - a plurality of interference components that are attached to the plurality of conduit connectors, respectively, and do not interfere with the plurality of conduit connectors in correct connection combination but selectively interfere with each of the conduit connectors in wrong connection combination to interrupt connection.

2. The insertion-instrument conduit connection device according to example 1, wherein
   - the plurality of fluid circulation conduits include at least three fluid circulation conduits including a first fluid circulation conduit, a second fluid circulation conduit, and a third fluid circulation conduit,
   - the plurality of conduit connectors include at least three conduit connectors of a first conduit connector, a second conduit connector, and a third conduit connector,
   - the first conduit connector provided at the first fluid circulation conduit and the second conduit connector provided at the second fluid circulation conduit have orientations different from each other or have configurations different from each other, and
   - the second conduit connector and the third conduit connector provided at the third fluid circulation conduit have the same orientation or have the same configuration.

3. The insertion-instrument conduit connection device according to example 2, wherein each of the plurality of conduit connectors is constituted by a pair of a connection body and a connection counterpart body that is connected to the connection body.

4. The insertion-instrument conduit connection device according to example 3, wherein the connection body is a male plug and the connection counterpart body is a female plug.

5. The insertion-instrument conduit connection device according to example 3, wherein
   - each of the interference components includes
     - a fixation member that adjacently holds and fixes the connection body of the first conduit connector and the connection counterpart body of the second conduit connector in parallel, and an interference member that is provided at the connection body of the third conduit connector and interrupts connection of one of the first conduit connector and the second conduit connector when another of the first conduit connector and the second conduit connector is connected to the third conduit connector, and an outer shape of the interference member is larger than an outer shape of the connection body or the connection counterpart body.

6. The insertion-instrument conduit connection device according to example 5, wherein the fixation member is provided with a plurality of holes into which the first and second fluid circulation conduits or the first and second conduit connectors are inserted, and the interference member is provided with a hole into which the third fluid circulation conduit or the third conduit connector is inserted.

7. The insertion-instrument conduit connection device according to example 6, wherein the fixation member is provided with grooves extending from an outer surface to the holes.

8. The insertion-instrument conduit connection device according to example 3, wherein each of the interference components includes a fixation member that adjacently holds and fixes the connection body of the first conduit connector, the connection counterpart body of the second conduit connector, and the connection counterpart body of the third conduit connector in parallel, and an interference member that is provided at the connection body of the third conduit connector and interrupts connection of one of the first conduit connector and the second conduit connector when another of the first conduit connector and the second conduit connector is connected to the third conduit connector, and an outer shape of the interference member is larger than an outer shape of the connection body or the connection counterpart body.

9. The insertion-instrument conduit connection device according to example 8, wherein the fixation member is provided with a plurality of holes into which the first and second fluid circulation conduits or the first and second conduit connectors are inserted, and the interference member is provided with a hole into which the third fluid circulation conduit or the third conduit connector is inserted.

10. The insertion-instrument conduit connection device according to example 9, wherein the fixation member is provided with grooves extending from an outer surface to the holes.

11. The insertion-instrument conduit connection device according to example 8, wherein an interval is provided between the first or second conduit connector fixed by the fixation member and the third connector, the interval having a size with which the connection is not interrupted by the interference member.

12. The insertion-instrument conduit connection device according to example 8, wherein the fixation member has an angle between a part that fixes the first or second conduit connector and a part that fixes the third conduit connector, the angle having a size with which the connection is not interrupted by the interference member.

13. The insertion-instrument conduit connection device according to example 1, wherein the plurality of fluid circulation conduits include at least two fluid circulation conduits including a first fluid circulation conduit and a second fluid circulation conduit, a first conduit connector provided at the first fluid circulation conduit and a second conduit connector provided at the second fluid circulation conduit have the same orientation or the same configuration, each of the first and second conduit connectors is constituted by a connection body and a connection counterpart body that is connected to the connection body, and each of the interference components includes a fixation member that adjacently holds and fixes the connection body of the first conduit connector and the connection body of the second conduit connector in parallel, and an interference member that adjacently holds and fixes the connection counterpart body of the first conduit connector and the connection counterpart body of the second conduit connector in parallel and does not interfere with the first and second conduit connectors in correct connection combination but collides with part of the fixation member in wrong connection combination to interrupt connection.

14. The insertion-instrument conduit connection device according to example 13, wherein the plurality of fluid circulation conduits additionally include a third fluid circulation conduit, and the first and second conduit connectors and a third conduit connector provided at the third fluid circulation conduit have orientations different from each other or configurations different from each other.

15. The insertion-instrument conduit connection device according to example 1, wherein each of the plurality of conduit connectors is a connector including a Luer taper.

16. The insertion-instrument conduit connection device according to example 2, wherein the first and third conduit connectors have opposite relationships of the connection body and the connection counterpart body to the second conduit connector when connected to each of the fluid circulation conduits at a distal end side and a proximal end side.

17. The insertion-instrument conduit connection device according to example 5, wherein the interference member is provided at the connection counterpart body of the third conduit connector.

18. The insertion-instrument conduit connection device according to example 3, wherein at least one of the plurality of fluid circulation conduits has a different position in a longitudinal direction of each of the conduit connectors with respect to another of the fluid circulation conduits.

19. An endoscope apparatus comprising:

an endoscope;

a plurality of fluid circulation conduits connecting the endoscope and an external fluid circulation device;

a plurality of conduit connectors attached to respective relay parts of the plurality of fluid circulation conduits; and a plurality of interference components that are attached to the plurality of conduit connectors, respectively, and selectively interfere with the conduit connectors by not interfering with the plurality of fluid circulation conduits in correct connection combination but interfering with the fluid circulation conduits in wrong connection combination to interrupt connection.

20. The endoscope apparatus according to example 19, wherein the endoscope is a single-use endoscope that is discarded after being used once.

What is claimed is:

1. A conduit connection device, comprising:
- a plurality of fluid circulation lines, the plurality of fluid circulation lines including a first fluid circulation line having a first conduit, a second fluid circulation line having a second conduit, and a third fluid circulation line having a third conduit;
- a plurality of relay fluid circulation lines, each of the plurality of relay fluid circulation lines having a relay fluid conduit;
- a plurality of conduit connectors, each of the plurality of conduit connectors having a connection body and a connection counterpart body forming a paired connection body; and
- a plurality of interference components,
- wherein a first connection body is located at a first end of the first fluid circulation line, a second connection counterpart body is located at a first end of the second fluid circulation line, and a third connection body is located at a first end of the third fluid circulation line,
- wherein the plurality of interference components includes:
  - a fixation member that adjacently holds and fixes the first connection body and the second connection counterpart body in parallel, and
  - an interference member located at the third connection counterpart body,
- wherein, in a first connection combination, the paired connection body of each of the plurality of conduit connectors includes the connection body releasably connected to the connection counterpart body, and
- wherein, in other than the first connection combination:
  - when the third connection counterpart body is connected to the first connection body, the interference member prevents the second connection body being connected to the second connection counterpart body, and
  - when the second connection body is connected to the second connection counterpart body, the interference member prevents the third connection counterpart body being connected to the first connection body.

2. The conduit connection device of claim 1, wherein a second end of each of the plurality of fluid circulation lines is attached to an insertion instrument, and
- wherein a second end of each of the plurality of relay fluid circulation lines is configured to attach to an external fluid circulation device.

3. The conduit connection device of claim 1, wherein, in the first connection combination and when a second end of each of the plurality of relay fluid circulation lines is attached to an external fluid circulation device and a second end of each of the plurality of fluid circulation lines is attached to an insertion instrument, the connected relay fluid circulation line and fluid circulation line provide a flow path for fluid communication between the external fluid circulation device and the insertion instrument.

4. The conduit connection device according to claim 3,
- wherein the fixation member adjacently holds and fixes the first connection body, the second connection counterpart body, and the third connection body in parallel, and
- wherein an outer shape of the interference member is larger than an outer shape of the first connection body or the second connection counterpart body.

5. The conduit connection device according to claim 4, wherein the fixation member is provided with a plurality of holes into which the first fluid circulation line and the second fluid circulation line are inserted or into which the first connection body and the second connection counterpart body are inserted, and
- wherein the interference member is provided with a hole into which the third fluid circulation line or the third connection counterpart body is inserted.

6. The conduit connection device according to claim 4, wherein the fixation member includes a plurality of grooves extending from an outer surface of the fixation member into which the first fluid circulation line and the second fluid circulation line are inserted or into which the first connection body and the second connection counterpart body are inserted, and
- wherein the interference member is provided with a groove extending from an outer surface of the interference member into which the third fluid circulation line or the third connection counterpart body is inserted.

7. The conduit connection device according to claim 4, wherein an interval is provided between (i) the first connection body or the second connection counterpart body fixed by the fixation member and (ii) the third connection body, and wherein the interval has a size such that a connection of a third conduit connector and the third connection counterpart body is not interrupted by the interference member.

8. The conduit connection device according to claim 4, wherein the fixation member has an angle between a first part that fixes the first connection body and the second connection counterpart body and a second part that fixes the third connection body, the angle having a size such that a connection of a third conduit connector and the third connection counterpart body is not interrupted by the interference member.

9. The conduit connection device according to claim 1, wherein:
- the first connection body has a first orientation, the second connection body has a second orientation, and the third connection body has a third orientation,
- the first orientation is different from the second orientation, and
- the second orientation is the same as the third orientation, or
- the first connection body has a first configuration, the second connection body has a second configuration, and the third connection body has a third configuration,
- the first configuration is different from the second configuration, and
- the second configuration is the same as the third configuration.

10. The conduit connection device according to claim 1, wherein the connection body of each of the plurality of conduit connectors is a male plug and the connection counterpart body of each of the plurality of conduit connectors is a female plug.

11. The conduit connection device according to claim 1, wherein an outer shape of the interference member is larger than an outer shape of the first connection body or the second connection counterpart body.

12. The conduit connection device according to claim 11, wherein the fixation member is provided with a plurality of holes into which the first fluid circulation line and the second fluid circulation line are inserted or into which the first connection body and the second connection counterpart body are inserted, and wherein the interference member is provided with a hole into which the third fluid circulation line or the third connection counterpart body is inserted.

13. The conduit connection device according to claim 12, wherein the fixation member includes a plurality of grooves extending from an outer surface of the fixation member into which the first fluid circulation line and the second fluid circulation line are inserted or into which the first connection body and the second connection counterpart body are inserted, and wherein the interference member is provided with a groove extending from an outer surface of the interference member into which the third fluid circulation line or the third connection counterpart body is inserted.

14. The conduit connection device according to claim 1, wherein each of the plurality of conduit connectors is a connector including a Luer taper.

15. An endoscope apparatus, comprising:

an endoscope; and the conduit connection device according to claim 1.

* * * * *